US009144522B2

(12) United States Patent
Ostertag

(10) Patent No.: US 9,144,522 B2
(45) Date of Patent: Sep. 29, 2015

(54) INCONTINENCE ARTICLE IN PANTS FORM

(75) Inventor: Wolfgang Ostertag, Gersetten (DE)

(73) Assignee: PAUL HARTMANN AG, Heidenheim (DE)

( * ) Notice: Subject to any disclaimer, the term of this patent is extended or adjusted under 35 U.S.C. 154(b) by 271 days.

(21) Appl. No.: 13/578,509

(22) PCT Filed: Feb. 2, 2011

(86) PCT No.: PCT/EP2011/000466
§ 371 (c)(1),
(2), (4) Date: Aug. 10, 2012

(87) PCT Pub. No.: WO2011/098226
PCT Pub. Date: Aug. 18, 2011

(65) Prior Publication Data
US 2012/0310193 A1 Dec. 6, 2012

(30) Foreign Application Priority Data
Feb. 13, 2010 (DE) .................. 10 2010 007 872

(51) Int. Cl.
*A61F 13/496* (2006.01)
*B32B 38/00* (2006.01)
(Continued)

(52) U.S. Cl.
CPC ..... *A61F 13/49011* (2013.01); *A61F 13/15593* (2013.01); *A61F 13/505* (2013.01); *A61F 2013/49025* (2013.01); *A61F 2013/49038* (2013.01); *Y10T 156/1049* (2015.01)

(58) Field of Classification Search
CPC ...... A61F 13/492; A61F 13/496; B32B 38/00

USPC ........................... 604/365; 156/226
See application file for complete search history.

(56) References Cited

U.S. PATENT DOCUMENTS 4,492,608 A 1/1985 Hirsch et al.
4,795,451 A 1/1989 Buckley
(Continued)

FOREIGN PATENT DOCUMENTS

DE 10 2007 056 126 A1 5/2009
DE 10 2007 063 209 A1 6/2009
(Continued)

*Primary Examiner* — Tatyana Zalukaeva
*Assistant Examiner* — Sara Sass
(74) *Attorney, Agent, or Firm* — Henry M. Feiereisen LLC.

(57) ABSTRACT

An incontinence article in pants form for receiving bodily excretions, includes an abdominal section, a back portion and a crotch portion which extends in the longitudinal direction between the abdominal and back sections and is undetachably joined in overlapping regions to the abdominal portion and the back portion, wherein the abdominal portion and the back portion are connected to one another on both sides at the lateral seam regions forming a closed waist opening. The crotch portion extends with the long end thereof on the abdominal side and with the long end thereof on the back side to a respective imaginary line L1 or L2 which is parallel to the transverse direction, wherein the lines L1 and L2 divide the abdominal portion and the back portion into a respective first abdominal or back sub-region remote from the leg opening and a respective second stomach or back sub-region near the leg opening. In the first abdominal and back sub-region, first elastification means are provided, of which in each case only one single first elastification means is fixed within a respective adhesive zone of the strip-shaped adhesive zones disposed in parallel at a distance M between a first and a second layer of the first abdominal and back sub-region.

13 Claims, 9 Drawing Sheets

(51) Int. Cl.
*A61F 13/49* (2006.01)
*A61F 13/15* (2006.01)
*A61F 13/505* (2006.01)

(56) References Cited

U.S. PATENT DOCUMENTS

| | | | |
|---|---|---|---|
| 5,507,909 | A | 4/1996 | Rollins et al. |
| 6,755,808 | B2 | 6/2004 | Balogh et al. |
| 7,118,558 | B2 | 10/2006 | Wu et al. |
| 7,335,273 | B2 | 2/2008 | Neculescu et al. |
| 7,642,398 | B2 | 1/2010 | Järpenberg et al. |
| 8,016,806 | B2 | 9/2011 | Hornung et al. |
| 8,025,652 | B2 * | 9/2011 | Hornung et al. ............ 604/385.3 |
| 8,100,173 | B2 | 1/2012 | Hornung et al. |
| 9,011,405 | B2 * | 4/2015 | Gassner et al. ............ 604/385.3 |
| 2001/0030014 | A1 | 10/2001 | Kwok |
| 2002/0007172 | A1 * | 1/2002 | Takei et al. ............ 604/385.27 |
| 2003/0082340 | A1 | 5/2003 | McCabe et al. |
| 2004/0182499 | A1 | 9/2004 | Collier, IV et al. |
| 2006/0064069 | A1 | 3/2006 | Rajala et al. |
| 2006/0142728 | A1 | 6/2006 | Tabor et al. |
| 2009/0178755 | A1 | 7/2009 | Hornung et al. |
| 2009/0240229 | A1 * | 9/2009 | Malowaniec ............ 604/385.28 |

FOREIGN PATENT DOCUMENTS

| | | |
|---|---|---|
| EP | 0 172 037 A1 | 2/1986 |
| EP | 0 405 575 A1 | 1/1991 |
| EP | 1 938 777 A2 | 6/2001 |
| EP | 1 327 430 A2 | 7/2003 |
| EP | 1 830 770 A1 | 9/2007 |
| JP | 2009-148447 | 9/2009 |
| WO | WO 99/27480 A1 | 7/1999 |
| WO | WO 03/039422 A1 | 5/2003 |
| WO | WO 03/039423 A1 | 5/2003 |
| WO | WO 2004/052260 A1 | 6/2004 |
| WO | WO 2009/065499 A1 | 5/2009 |
| WO | WO 2009/080180 A1 | 7/2009 |

* cited by examiner

INCONTINENCE ARTICLE IN PANTS FORM

CROSS-REFERENCES TO RELATED APPLICATIONS

This application is the U.S. National Stage of International Application No. PCT/EP20111/000466, filed Feb. 2, 2011, which designated the United States and has been published as International Publication No. WO 2011/098226 A1 and which claims the priority of German Patent Application, Serial No. 10 2010 007 872.7, filed Feb. 13, 2010, pursuant to 35 U.S.C. 119(a)-(d).

BACKGROUND OF THE INVENTION

The invention relates to an incontinence article in the form of pants for receiving bodily excretions, with a front stomach portion and a rear back portion which, in order to form a stomach and back band that is continuous in the transverse or waist-encircling direction and has a waist opening closed in the waist-encircling direction, are connected to each other by the manufacturer at side seam regions on both sides, and with a crotch portion which has an absorbent body and which extends in a longitudinal direction between stomach portion and back portion and is joined inseparably to the stomach portion and to the back portion, wherein not only the crotch portion but also the stomach portion and the back portion delimit the leg openings of the incontinence article. An incontinence article of this kind composed of three components is known, for example, from WO 2004/052260 A1, WO 03/039423 A1 and WO-2009/065499 A1. In the case of this specific product concept, after the joining of the crotch portion, extending in the longitudinal direction, to the stomach portion, extending substantially in the transverse or waist-encircling direction, and to the back portion, extending correspondingly, in the spread-out flat state of these three components, an H-shaped basic structure of the incontinence article can be produced. The incontinence article is then formed in a modular manner from the components crotch portion, stomach portion and back portion. These components are advantageously first connected to one another by way of the crotch portion, and, preferably, the stomach portion is thereafter connected to the back portion in side seam regions on both sides. This is a connection performed at the manufacturer's, by which the pants shape is obtained. This connection is typically inseparable. The pants shape may, however, also be separable, in particular along a predetermined breaking line, which may in particular run in the side seam region, for example for removing a used incontinence article from a person needing care.

Incontinence articles in pants form are different in principle from traditional openable and closable incontinence articles in the customary diaper form in that the waist size is generally predetermined and the adaptation to different body sizes is achieved on the basis of a number of standard sizes by an elastic stretchability of the article. Generally used for this purpose are elasticating means, in particular in the form of bands or threads, often referred to as Lycra threads, connected in the pre-stretched state (stretch-bonding process) to chassis materials of the incontinence article, that is to say they are fixed in the pre-stretched state to the chassis materials, for example by means of an adhesive. As a result of their pretensioning, these elasticating means gather the chassis materials together and thereby form pleatings. The incontinence article or the elasticated chassis materials of the incontinence article can then stretch again elastically when the incontinence article is put onto the user like a pair of pants. Incontinence articles in pants form with such elasticated chassis materials are known in many instances and, for example, are also discussed in the previously mentioned WO 2004/052260 A1 and WO-2009/065499-A1.

Using the present invention made it possible to identify that there nevertheless may be significant forces acting in the process of putting on the incontinence article in pants form, to be precise when the chassis materials which were gathered together under the pretension of the elasticating means is opened out. These forces act from different directions, depending, inter alia, on the process of putting on by the individual user. Thus, the forces can act in parallel with and/or at an angle to the profile of the elasticating means and, accompanying this, on the whole laminate structure made of elasticating means and chassis material. The incontinence article in pants form is predominantly exposed to the force action in the region of the waist opening by being pulled apart in the transverse or waist-encircling direction by the user, for example to identify the leg openings for getting into the incontinence article but then also by the chassis material being gripped in order to pull up the incontinence article along the body of the user, and also during this process. This can disadvantageously lead to an impairment of the hold between elasticating means and chassis material right up to a partial delamination, and so the areal elasticating effect of the chassis materials is impeded and hence the fit of the incontinence article in pants form is adversely affected.

Likewise, using the present invention made it possible to identify that the attachment of the elasticating means provided on a chassis material should be adapted to the functions and the objects of the elasticated region in order thus to ensure a very comfortable wear for the user.

Within usual methods, a measure for attaching elasticating means on chassis materials lies in the use of adhesives. Various methods for adhesively attaching elasticating means are known. Thus, EP 1 938 777 A2 describes applying glue to the whole area of at least one of the non-woven fabric webs provided for sandwich-positioning of elasticating means and how these are brought together while laminating an elastic material therein. Disadvantageously, applying glue to the whole area results in large-scale stiffening and a reduction in the breathability of materials, in particular of non-woven fabric materials which are soft and breathable per se, and which are usually used for incontinence articles.

It is furthermore known to carry out single-strand gluing, to be precise such that individual elasticating means are initially surrounded by adhesive and thereafter fed to the lamination between two material webs. Thus, WO 2003/039422 A1 the individual elasticating means is led through a comb-like groove shape of an adhesive application head. Although this counteracts the problem of excessive stiffening and an excessive reduction in the breathability of the chassis materials, a disadvantage in this case nevertheless lies in the fact that the connection points for obtaining a laminate made of elasticating means and chassis material are only obtained at the circumference of the elasticating means. Thus, sufficient holding together of the laminate can only be achieved by a sufficiently large number of elasticating means per material portion. It may likewise be disadvantageous in this case that as a result of the direct application of the adhesive on the elasticating means there is an increase in the risk of damage to the elasticating means. Moreover, it is difficult in the case of single-strand gluing to set the amount of adhesive that should be transferred onto an elasticating means, more particularly onto a thread-shaped elasticating means. Moreover, EP-1830770-A1 also suggests affixing, by means of single-strand gluing, elastic threads arranged in the transverse direction. WO 2009/080180 A1 also provides for individually coating the elasticating means, which run parallel in the transverse direction, with an adhesive.

SUMMARY OF THE INVENTION

Proceeding from this, the object of the present invention is to counteract the problems described above, that is to say in particular to form a stable connection between the chassis materials, which form the stomach portion and the back portion, and the thread-like elasticating means to be fixed thereto in an incontinence article of the type in question, without this adversely affecting the wearing comfort or having further consequences impairing the functionality of the incontinence article.

This object is achieved according to the invention by an incontinence article with a front stomach portion and a rear back portion which, in order to form a stomach and back band that is continuous in the transverse or waist-encircling direction and has a waist opening closed in the waist-encircling direction, are connected to each other by the manufacturer at side seam regions on both sides, and with a crotch portion which has an absorbent body, wherein the crotch portion, having a stomach-side long end and a back-side long end, extends in a longitudinal direction between the stomach portion with a crotch-facing transverse periphery and the back portion with a crotch-facing transverse periphery, and wherein the stomach-side long end extends in the longitudinal direction as far as an imaginary line L2 running parallel to the transverse direction, and wherein the crotch portion overlaps the stomach portion in a front overlapping region and is joined inseparably to the stomach portion, and wherein the crotch portion overlaps the back portion in a rear overlapping region and is joined inseparably to the back portion, wherein the crotch portion comprises a liquid-impermeable backsheet material and a topsheet material, and wherein the absorbent body is arranged between backsheet material and topsheet material, wherein the topsheet material and/or the backsheet material form an overhang that extends outside longitudinal peripheries of the absorbent body, wherein not only the crotch portion but also the stomach portion and the back portion delimit the leg openings of the incontinence article, wherein the line L1 divides the stomach portion into a first stomach subregion away from the leg openings and a second stomach subregion near the leg openings, and the line L2 divides the back portion into a first back subregion away from the leg openings and a second back subregion near the leg openings, wherein first thread-like or band-like elasticating means with a thread diameter D are provided in the first stomach subregion and in the first back subregion and extend at a distance N from one another, and parallel to one another, in the transverse or waist-encircling direction and thus elasticate the first stomach subreqion and the first back subregion across the surface areas thereof, wherein the first stomach subregion and the first back subregion each have at least a first layer and a second layer between which the first elasticating means are secured by strip-shaped adhesive zones, wherein the strip-shaped adhesive zones, running parallel in the transverse direction or waist-encircling direction (16) and with a width G, are arranged at a distance M from one another, wherein the width G of the strip-shaped adhesive zones is greater than the thread diameter D of the first elasticating means, and wherein a single first elasticating means is in each case arranged within one respective strip-shaped adhesive zone.

Advantageous developments of the incontinence article are provided by the respective subclaims.

The object is achieved, in an incontinence article with a three-component structure, by the inventive arrangement of the elasticating means and of the adhesive zones.

The incontinence article in the form of pants for receiving bodily excretions has a front stomach portion and a rear back portion which, in order to form a stomach and back band that is continuous in the transverse or waist-encircling direction and has a waist opening closed in the waist-encircling direction, are connected to each other by the manufacturer at side seam regions on both sides.

The incontinence article also has a crotch portion, which has an absorbent body.

The crotch portion comprises a liquid-impermeable backsheet material and a topsheet material, wherein the absorbent body is arranged between backsheet material and topsheet material. The topsheet material and/or the backsheet material form, in the transverse direction, an overhang that extends outside longitudinal peripheries of the absorbent body.

The crotch portion, having a stomach-side long end and a back-side long end, extends in a longitudinal direction between the stomach portion with a crotch-facing transverse periphery and the back portion with a crotch-facing transverse periphery.

The crotch portion overlaps the stomach portion in a front overlapping region and is joined inseparably to the stomach portion, and the crotch portion overlaps the back portion in a rear overlapping region and is joined inseparably to the back portion.

Not only the crotch portion but also the stomach portion and the back portion delimit the leg openings of the incontinence article.

The stomach-side long end of the crotch portion extends in the longitudinal direction as far as an imaginary line L1 running parallel to the transverse direction, and the back-side long end of the crotch portion extends in the longitudinal direction as far as an imaginary line L2 running parallel to the transverse direction.

The line L1 divides the stomach portion into a first stomach subregion away from the leg openings and a second stomach subregion near the leg openings, and the line L2 divides the back portion into a first back subregion away from the leg openings and a second back subregion near the leg openings.

First thread-like or band-like elasticating means with a thread diameter D are provided in the first stomach subregion and in the first back subregion and extend at a distance N from one another, and parallel to one another, in the transverse or waist-encircling direction and thus elasticate the first stomach subregion and the first back subregion across the surface areas thereof.

The first stomach subregion and the first back subregion each have at least a first layer and a second layer between which the first elasticating means are secured by strip-shaped adhesive zones.

The strip-shaped adhesive zones, running parallel in the transverse direction or waist-encircling direction and with a width G, are arranged at a distance M from one another. The width G of the strip-shaped adhesive zones is greater than the thread diameter D of the first elasticating means, and a single first elasticating means is in each case arranged within one respective strip-shaped adhesive zone.

The parallel and spaced-apart arrangement of strip-shaped adhesive zones results in the formation of stable laminate structures of first thread-like or band-like elasticating means with the chassis materials, that is to say of a first layer and a second layer, between which the first elasticating means are arranged. The fact that the width of the strip-shaped adhesive zone is greater than the thread diameter of the single thread-like or band-like first elasticating means within the strip-shaped adhesive zone results, on the one hand, in a secure fixing of the first elasticating means and also, on the other hand, in a direct fixing of the two layers to each other, namely by the remaining area of the adhesive zone not covered by the first elasticating means. This is advantageous over a single strand of glue, which permits a connection between material layer and elasticating means only along the circumference of the elasticating means. Despite secure lamination of first elasticating means to the two layers adjoining the first elasticating means and embedding the latter, the distances between the strip-shaped adhesive zones ensure that the wearing comfort for the user is maintained or adjusted. On the one hand, the breathing activity of the chassis materials is impaired only to a lesser extent than if the entire surface area is glued. On the other hand, through the choice of the width and the distances of the strip-shaped adhesive zones, it is possible to adjust the stability that is required for the pants-shaped incontinence article and also the wearing comfort desired by the user. In the specialist field of incontinence articles, very thin materials are in fact used, for example thin nonwoven materials, which in most cases also have inherent properties such as softness, great flexibility and a high degree of breathability. However, this leads to a considerable lack of homogeneity, with a negative impact on the user, between the back portion and stomach portion in terms of the properties described above, as is explained here. It is true that a large overhang of the topsheet material and/or of the backsheet material in the transverse direction outside the longitudinal peripheries of the absorbent body, and if appropriate also in the longitudinal direction outside the transverse peripheries of the absorbent body, has the advantage that, because of the large overlapping region between crotch portion and stomach portion or between crotch portion and back portion, the crotch portion can be securely fixed by the manufacturer to the back portion and stomach portion, in particular by means of adhesives. However, it has been found that, because of the large number of layers compared to the area outside the contour of the crotch portion, the overlapping region is excessively stiffened. This substantial, abrupt and unexpected change of property of the back portion and stomach portion, resulting from design considerations and taking place at the longitudinal peripheries and, if appropriate, at the transverse peripheries of the crotch portion, is felt by the user to be a disadvantage, since the incontinence article in this way differs significantly from normal underwear. By securing the first elasticating means using strip-shaped adhesive zones in the manner described in claim 1, the area of the back portion and stomach portion lying outside the contour of the crotch portion can be moderately stiffened in such a way that the abrupt and unexpected change of property occurring at the longitudinal peripheries and, if appropriate, at the transverse peripheries of the crotch portion is less noticeable to the user, and the incontinence article in this respect gives the impression of normal underwear.

With the aforementioned features, an incontinence article in the form of pants and having the three-component structure is thus created in which the components can be securely connected, without this impairing the wearing comfort or the functionality of the incontinence article or of its components, but instead improving the wearing comfort.

A further object of the present invention is to make available a method for producing an incontinence article in the form of pants having the features mentioned at the outset, which method takes account in particular of the aspects mentioned above, in particular a stable connection between the chassis materials, which form the stomach portion and the back portion, and the thread-like or band-like elasticating means to be secured thereon, while maintaining the wearing comfort and functionality.

This object is achieved by a method for producing an incontinence article of this kind, with the method steps of supplying two subsidiary webs, each forming one of a first layer of a first back subregion of a back portion of the incontinence article and a first layer of a first stomach subregion of a stomach portion of the incontinence article; supplying another two subsidiary webs, each forming one of a second layer of the first back subregion of the incontinence article and a second layer of the first stomach subregion of the incontinence article, wherein the first back subregion is adiacent to a second back subregion of the back portion, and the first stomach sub regions adjacent to a second stomach subregion of the stomach portion, wherein the first and second back subregions are defined by a first imaginary line and the first and second stomach sub regions are defined by a second imaginary line, wherein the first back subregion and the first stomach subregion are distal from leg openings of the incontinence article and wherein the second back subregion and the second stomach subregion are proximate to the leg openings; applying an adhesive coating in the form of strip-shaped adhesive zones to at least one of the subsidiary webs which respectively form the first and second layers of the back subregion and to at least one of the subsidiary webs which respectively form the first and second layers of the stomach subregion, wherein said adhesive zones are applied in parallel relationship and at a first distance to one another and are defined by a width; supplying first elasticating means in a machine direction in parallel relationship and at a second distance to one another, wherein the elasticating means have a thread diameter, wherein the second distance is greater than the first distance; placing one of the first elasticating means in the machine direction within each one of the adhesive zones onto the at least one of the subsidiary webs which respectively form the first and second layers of the back subregion and onto the at least one of the subsidiary webs which respectively form the first and second layers of the stomach subregion; connecting the first elasticating means with the two subsidiary webs and the another two subsidiary webs; supplying crotch portions, wherein each of the crotch portions includes an absorbent body, a liquid-impermeable backsheet material and a topsheet material, and has opposing ends, wherein the absorbent body is arranged between the backsheet material and the topsheet material, wherein the topsheet material and/or the backsheet material form an overhang which extends outside of longitudinal peripheries of the absorbent body; bringing the crotch portions together with the subsidiary webs which respectively form the back subregion and the subsidiary webs which form the stomach subregion so that the crotch portions are arranged in a longitudinal direction which is transverse to the machine direction, and one of the opposing ends is arranged plan in a front overlapping region of the subsidiary webs which respectively form the first and second layers of the back subregion and extends up to the first imaginary line and the other opposing end is arranged plan in a rear overlapping region of the subsidiary webs which respectively form the first and second layers of the stomach subregion and extends up to the second imaginary line, and wherein the crotch portions are arranged spaced apart from one another in the machine direction; fixing the crotch portions to the subsidiary webs which respectively form the first and second layers of the back subregion and to the subsidiary webs which respectively form the first and second layers of the stomach subregion in the front and rear overlapping regions; folding the crotch portions about a fold line which runs in the machine direction, so that the subsidiary webs which respectively form the first and second layers of the back subregion come to lie over the subsidiary webs which respectively form the first and second layers of the stomach subregion; joining the subsidiary webs which respectively form the first and second layers of the back subregion to the subsidiary webs which respectively form the first and second layers of the stomach subregion in a direction transverse to the machine direction at defined distances along the machine direction to form side seam regions of the incontinence article; cutting the joined subsidiary webs transversely with respect to the machine direction to obtain finished individual ones of the incontinence article, wherein the crotch portion, the stomach portion and the back portion delimit the lea openings of the incontinence article, and wherein the stomach portion and the back portion are connected to each other at two of said side seam regions to form a stomach- and back band which is continuous in a waist-encircling direction of the incontinence article thereby defining a waist opening.

The absolute figures given for lengths and/or widths of the incontinence article as such or of the components thereof, for example stomach portion, back portion and crotch portion, and also of the strip-shaped adhesive zones or adhesive-zone portions, are always based on dimensions on the incontinence article in its laid-out flat, stretched and spread-out state.

The spacing M between parallel, strip-shaped adhesive zones is measured by the distance of the peripheries, extending directly adjacently in the transverse direction, from two directly adjacent adhesive zones. The spacing N between parallel first elasticating means is determined analogously, i.e. the distance between the two directly adjacent first elasticating means is measured. The spacing P between adhesive-zone portions spaced apart in the transverse direction is measured by the distance of the peripheries, extending directly adjacently in the longitudinal direction, from two directly adjacent adhesive-zone portions.

By contrast, the thread diameter D of the first elasticating means is based on the unstretched, relaxed state of the first elasticating means.

Knowing the material properties of the first elasticating means used, namely thread thickness and density $\rho$, the thread diameter D can be calculated using the following formula:

$$D = 2 \times \text{radius } r = 2 \times \sqrt{\frac{\text{thread strength}}{\Pi \cdot \text{density } \rho}}$$

The thread thickness is understood as the mass relative to the running length and is expressed by the unit dtex, with 1 dtex=1 g/10,000 m. The density $\rho$ as a ratio of the mass to the volume is expressed by the SI unit kg/m3.

In the case of a first elasticating means that does not have a circular diameter but instead has a band-like appearance, the greatest extent between the outer peripheries of the elasticating means is used as thread diameter D.

In the quotients G/M, G/D and S/P described in more detail below, the parameter in the numerator is divided by the parameter in the denominator. These are quotients in which width B, distance M, length S or distance P are related to one another. It is assumed here that only values with the same dimensional unit are included in the numerator and denominator, resulting in a quotient without unit.

Advantageously, the topsheet material and/or the backsheet material can also form, in the longitudinal direction, an overhang that extends in each case outside transverse peripheries of the absorbent body.

"Overhang" is understood as meaning the extent of the topsheet material and/or of the backsheet material in the transverse direction laterally outside the longitudinal peripheries of the absorbent body or in the longitudinal direction outside the transverse peripheries of the absorbent body, the maximum extent being used in each case, that is to say the outer extent of the topsheet material and/or the backsheet material situated distally furthest from the longitudinal peripheries or from the transverse peripheries of the absorbent body. The backsheet material and/or the topsheet material may advantageously consist of a number of components, thus for example the topsheet material may advantageously be a composite of a topsheet material and barrier means adjacent on both sides in the longitudinal direction. It is therefore understood that, even in the case of composites, that is to say composed topsheet materials and/or backsheet materials in which the individual layers do not cover one another congruently, when considering the overhang, the maximum outer extent of the composite, or of the individual material layers occurring therein, that is to say the outer extent situated distally furthest away, is used in each case.

"Chassis materials" are understood as meaning the materials forming a shell of the entire incontinence article or of the individual components, and also of the stomach portion, the back portion and/or the crotch portion, for example the topsheet material and the backsheet material of the crotch portion or the at least first and second layer of the first and/or second stomach subregion and/or of the first and/or second back subregion.

According to the invention, the first elasticating means are applied only as a single elasticating means within a strip-shaped adhesive zone. Preferably, the first elasticating means are applied centrally within the strip-shaped adhesive zones. In this way, it is advantageously possible to achieve a uniform fixing of the first elasticating means within the adhesive zone and also a good mutual fixing of the first and second layers of the first stomach subregion and/or of the first back subregion by means of the region of the adhesive zone adjoining the first elasticating means.

In a development of the invention, it proves advantageous if, in the first stomach subregion away from the leg openings and/or in the first back subregion away from the leg openings, the width G of the strip-shaped adhesive zones is chosen in such a way, and the adhesive zones are arranged at a distance M in such a way, that the quotient G/M is at least 0.10, in particular at least 0.30, more particularly at least 0.50, more particularly at least 0.75, more particularly at least 1.0, preferably at most 7.5, more preferably at most 6.0, more preferably at most 5.0, more preferably at most 4.0. By means of this arrangement of the strip-shaped adhesive zones, defined by their width and their distance from one another, a stability of the composite of the first elasticating means with the chassis materials is achieved, without the composite being stiffened too much or being left too soft. Moreover, the use of excess use of adhesive materials and therefore also costs are avoided.

In a further advantageous development, the adhesive zones have a width G of 2-15 mm, more preferably of 2-12 mm, more preferably of 2-10 mm, more preferably of 2-8 mm, more preferably of 2-6 mm.

In a further advantageous development, the adhesive zones are arranged at a spacing M of 2-25 mm, more preferably of 2-20 mm, more preferably of 2-15 mm, more preferably of 2-10 mm, more preferably of 2-8 mm, more preferably of 2-6 mm.

More advantageously, the adhesive zones spaced apart and parallel in the longitudinal direction of the incontinence article can have a different width G. Particularly advantageously, the adhesive zones arranged in the direction of the line L1 or L2 have a smaller width G than the adhesive zones arranged in the direction of the waist opening. By means of the wider adhesive zones arranged in the direction of the waist opening, the force that occurs during fitting, and that acts on the first elasticating means arranged particularly in the area of the waist opening between the first and second layers, is taken into account and thus counteracted.

In a further advantageous development, the width G of the adhesive zone and the thread diameter D of the single first elasticating means arranged therein are chosen such that the quotient G/D is at least 2, more preferably at least 4, more preferably at least 6, more preferably at least 8, more preferably at least 10, but preferably at most 100, more preferably at most 80, more preferably at most 60, more preferably at most 50, more preferably at most 40, more preferably at most 30. Through the coordinated choice of the width G of the adhesive zone and of the thread diameter D of the single elasticating means arranged in the adhesive zone, it is possible to achieve optimal embedding of the first elasticating means within the width of the adhesive zone and an optimal extent of a region of the adhesive zone not covered by the first elasticating means, which region allows the first and second layers to be fixed to each other.

The first thread-like or band-like elasticating means are preferably rubber or polyether-polyurethane or polyester-polyurethane threads, preferably elastic threads such as Lycra®, Creora® or Spandex® threads.

The first thread-like or band-like elasticating means preferably have a strength of 300-1500 dtex, particularly of 500-900 dtex, more particularly of 500-600 dtex.

The first thread-like or band-like elasticating means preferably have a thread diameter D of 0.05-1.0 mm, more preferably 0.05-0.8 mm, more preferably 0.05-0.6 mm, more preferably 0.05-0.5 mm, more preferably 0.05-0.4 mm, more preferably 0.05-0.3 mm.

The first elasticating means are fixed in the stretched state to the chassis materials, that is to say between the first and second layers of the first stomach subregion and between the first and second layers of the first back subregion.

The first elasticating means are preferably fixed with a pretensioning of 1.5-6.0, particularly of 2.5-5.0 on the chassis-forming shell materials of the stomach portion and back portion, that is to say between the first and second layers of the first stomach subregion and back subregion away from the leg openings. The pretensioning is defined here as a factor of the degree of stretching with respect to the unstretched/relaxed state of the elasticating means.

The first elasticating means in the first stomach subregion away from the leg openings and/or in the first back subregion away from the leg openings preferably have the same pretensioning. However, it is possible that the first elasticating means in the direction of the waist opening have a greater pretensioning or that several of these elasticating means are provided at a smaller spacing from one another, in order to achieve slightly greater elastication in the region of the waist opening.

It has proven particularly advantageous if the distance N of the first elasticating means from one another (that is to say the distance between directly adjacent first elasticating means) is in particular 3-30 mm, more particularly 3-20 mm, more particularly 3 to 15 mm, more particularly 3 to 10 mm.

In a preferred embodiment, the strip-shaped adhesive zones in the first stomach subregion and in the first back subregion extend continuously and without spacing in the transverse direction. More preferably, the strip-shaped adhesive zones extend substantially over the entire transverse direction of the first stomach subregion and of the first back subregion.

"Substantially" means that the strip-shaped adhesive zones can end at a distance of at most 2% of the transverse extent of the stomach portion and/or of the back portion, more particularly at most 1% of the transverse extent of the stomach portion and/or of the back portion, before the respective lateral longitudinal peripheral portions of the stomach portion and of the back portion. More particularly, the strip-shaped adhesive zones end at most 8 mm, more particularly at most 5 mm, before the respective lateral longitudinal peripheral portions of the stomach portion and/or of the back portion.

In an alternative embodiment, the strip-shaped adhesive zones comprise adhesive-zone portions that are arranged at a spacing P in the transverse direction and have a length S.

More preferably, the strip-shaped adhesive zone portions having the length S are arranged at a spacing P in the transverse or waist-encircling-direction in such a way that the quotient S/P is at least 0.1, more preferably at least 0.3, more preferably at least 0.5, more preferably at least 1.0, more preferably at least 2.0, but more preferably at most 15, more preferably at most 13, more preferably at most 10. Through this arrangement of the strip-shaped adhesive zone portions, defined by their length and their mutual spacing, it is possible to achieve a sufficient stability of the composite of the first elasticating means with the chassis materials.

The arrangement of the spaced-apart adhesive zone portions is advantageously such that the mutual spacing P of the adhesive zone portions is at least not greater than the length S of the adhesive zone portions.

More preferably, the adhesive zone portions have a length S of at least 2 mm, more preferably of at least 5 mm, more preferably of at least 8 mm, more preferably of at least 10 mm, but preferably of at most 30 mm, more preferably of at most 25 mm, more preferably of at most 20 mm.

Preferably, the adhesive zone portions are arranged at a spacing P of at least 2 mm, more particularly of at least 4 mm, more particularly of at most 20 mm, more particularly of at most 15 mm, more particularly of at most 10 mm, more particularly of at most 8 mm.

The first stomach subregion away from the leg openings and the first back subregion away from the leg openings preferably occupy a proportion of 30-75%, more particularly of 35-70%, more particularly of 35-65%, relative to the surface area of the stomach portion and of the back portion.

The proportion of the surface area of the first stomach subregion away from the leg openings relative to the surface area of the stomach portion is advantageously greater than the proportion of the surface area of the first back subregion away from the leg openings relative to the surface area of the back portion. This is advantageous since, when putting an incontinence article on, the user takes hold in particular of the front region of the incontinence article, that is to say the stomach portion, and in particular the upper area oriented in the direction of the waist opening, that is to say the first stomach subregion away from the leg openings, in the chassis materials and the first elasticating means connected thereto.

According to the invention, the strip-shaped adhesive zones, viewed in the longitudinal direction of the incontinence article, are arranged at a distance M from one another. More preferably, the strip-shaped adhesive zones are arranged as adhesive zone portions with a spacing P in the transverse direction of the incontinence article.

Preferably, the first stomach subregion away from the leg openings or the first back subregion away from the leg openings has a surface free from adhesive zones or a surface free from adhesive zone portions, with a proportion of 20-80%, in particular of 25-70%, more particularly of 30-60%, relative to the surface area of the first stomach subregion or back subregion away from the leg openings. This proportion of surfaces free from adhesive zones (or adhesive zone portions) advantageously provides flexibility, which is pleasant for the user, and/or also breathability of the incontinence article, even though moderate stiffening is obtained.

The adhesive zones or adhesive zone portions have an adhesive coating.

The adhesive coating is in this case particularly preferably applied with a area density of 2-40 g/m2, more particularly 2-30 g/m2, more particularly 2-20 g/m2, more particularly 2-10 g/m2.

The adhesive coating comprises an adhesive, preferably a hotmelt adhesive, more particularly a hydrophobic hotmelt adhesive.

Examples of adhesives that can preferably be used are: D 9105 ZP or LC 3001 ZP (H. B. Fuller Deutschland GmbH, An der Roten Bleiche 2-3, 21335 Luneburg, Germany); H20028 or H 2481 (Bostik Nederland B. V., Zeggeveld 10, 4705 RP Roosendaal, Netherlands); Technomelt Q2415 or Technomelt Q5430 (Henkel KGaA, 40191 Düsseldorf, Germany).

The adhesive coating of the adhesive zone or of the adhesive zone portion is preferably provided across the entire surface within the adhesive zone or the adhesive zone portion.

The adhesive coating is applied to the mutually facing upper sides of the first and/or second layer of the first stomach subregion and on the mutually facing upper side of the first and/or second layer of the first back subregion. That is to say, the adhesive coating is applied at least to one of said first and second layers of the first stomach subregion and one of said first and second layers of the first back subregion.

In an advantageous embodiment, the adhesive coating is applied only to one of said first and second layers of the first stomach subregion and only to one of said first and second layers of the first back subregion. By applying the adhesive coating to only one of the first and second layers between which the first elasticating means is arranged, the process of application of the adhesive can be made technically easier.

In an alternative embodiment, the adhesive coating can be applied to the first and second layers of the first stomach subregion and/or of the first back subregion. In this case, the first and second layers are provided with a substantially congruent pattern of adhesive coating, which then come to lie on each other in the laminate arrangement with the first elasticating means placed in the middle. Through the provision of adhesive coating on both layers, the first elasticating means is formally embedded in an envelope of adhesive coating, which results in very good fixing of the first elasticating means to the first and second layers. The aforementioned negative effects of a single strand of glue are advantageously avoided in this way.

In this alternative embodiment, the amount of adhesive used per layer, that is to say the area density, can advantageously be reduced, in particular halved, by comparison with an adhesive coating on only one layer. However, it is entirely conceivable that the area density of the adhesive coating is different for the first and second layers. This can be dependent on the chassis materials used for the first and second layers.

The adhesive coating of the adhesive zone or of the adhesive zone portion can be applied by various methods known in the art, such as contact application methods, contactless application methods, for example also by spraying, onto the respective first and/or second layer of the first stomach subregion or of the first back subregion.

Preferably, the adhesive coating for producing the adhesive zones or adhesive zone portions is applied to the first and/or second layer of the first stomach subregion or of the first back subregion by a contact method. In the contact method, the corresponding first and/or second layers of the first stomach subregion and of the first back subregion are provided directly with strips of adhesive coating, by means of the glue applicator head and the chassis material being guided in a relative movement with respect to each other. With the contact method, the desired strip shape with the desired dimensions of the adhesive zone (width, spacing) can be obtained more advantageously compared to contactless methods, such as spraying, since the latter entails the risk of atomization of the adhesive and, consequently, a less precise application of the adhesive.

In a development of the invention, it proves advantageous if the front overlapping region of crotch portion to stomach portion occupies at least 12%, in particular 15-40%, more particularly 15-35% and more particularly 15-25% of the surface of the stomach portion, and the rear overlapping region from crotch portion to back portion occupies at least 20%, in particular 20-40%, more particularly 20-35% and more particularly 22-32% of the surface of the back portion.

Advantageously, the crotch portion overlaps the stomach portion with a surface of 25,000-45,000 mm2.

Advantageously, the crotch portion overlaps the back portion with a surface of 35,000-65,000 mm2, in particular 40,000-55,000 mm2.

The overlap of the crotch portion with the back portion is advantageously greater than the overlap of the crotch portion with the stomach portion.

According to the invention, the crotch portion and the stomach portion/back portion are joined inseparably to each other. It also proves particularly advantageous that the crotch portion can be connected to the stomach portion and/or to the back portion by means of adhesive not applied across the entire surface. It has in fact been found that, using adhesive not applied across the entire surface, the properties of the chassis materials are influenced to a lesser extent than if adhesive is applied across the entire surface in order to produce the connection between crotch portion and stomach portion and between crotch portion and back portion. An application of adhesive that is not over the entire surface may be, for example, a strip-shaped pattern, a web-shaped continuous or discontinuous grid structure, or insular regions, or else a strip-shaped or spirally arranged adhesive structure.

Particularly preferably, in the incontinence article in the form of pants, second elasticating means, in particular thread-like or band-like elasticating means, are also provided in the second stomach subregion near the leg openings and/or in the second back subregion near the leg openings, particularly in such a way that the second elasticating means continuously elasticate the respective second stomach subregion or back subregion.

The second elasticating means preferably extend from the two side seam regions of the second stomach subregion and/or of the second back subregion in the direction of a longitudinal center axis of the incontinence article and, particularly preferably, the second elasticating means run in an arcuately fanning-out manner with increasing distance from one another.

The second elasticating means are advantageously designed such that the restoring force occurring upon surface stretching of this second stomach subregion and/or of the second back subregion is less than when surface stretching takes place in the corresponding first stomach subregion or first back subregion, in which only the first elasticating means are provided. This ensures better wearing comfort of the incontinence article, because the incontinence article, in the respective region near the leg openings, can be stretched to a greater extent to match the body shape, without this at the same time causing an unpleasant increase in the restoring forces which, particularly if the user is very mobile, can lead to relative movements between the incontinence article and the user and can cause disagreeable or even medically problematic skin irritations.

The restoring force is the force with which the first or second stomach subregion or back subregion counters a surface stretching in the direction of the course of the first and/or second elasticating means.

To determine the restoring forces, the regions of the chassis material to be measured may be firmly clamped directly, as it were non-destructively, between two clamping jaws of a defined, identical clamping jaw width, and the restoring forces determined under defined stretching of the regions to be measured that simulates the state of use, by particularly 30% or 50% or 80% of the initial length (of the clamping jaw spacing when fixing the region to be measured in the unclamped state). The clamping jaws should fix as many elasticating means as possible, but at least two arranged next to one another, of the region to be measured and be oriented substantially perpendicularly with respect to the line followed by the elasticating means, so that the stretching takes place between the clamps substantially in the direction of the line followed by the elasticating means.

To this end, a region in the second stomach portion near the leg openings or in the second back portion near the leg openings, in which the second elasticating means fan open in the direction toward the longitudinal central axis, is preferably designed such that if this region is stretched in an areal manner, the restoring force arising in the process reduces in the direction toward the crotch portion. Thus, if one considers this second stomach portion and back portion near the leg openings, to be precise in a direction starting from the respective side seam region in the direction of the crotch portion, i.e. in the direction of a longitudinal central axis of the incontinence article and, effectively, in the direction of the arcuately fanning out of the second elasticating means, the restoring force arising in this direction in the case of areal stretching is reduced. Thus, this is the force with which the second stomach portion and the second back portion counteract areal stretching. A reduction in this restoring force, which is then naturally transferred to the user, is connected to a significant improvement in the wearing comfort of the incontinence article.

It has particularly proven to be advantageous if a minimum distance between the second elasticating means (spacing of elasticating means lying directly next to one another) in the side seam regions is 3 to 8 mm, particularly 3 to 7 mm and more particularly 3 to 6 mm.

Furthermore, it has proven to be advantageous if a maximum distance between the second elasticating means (spacing of elasticating means lying directly next to one another) at a periphery of the absorbent body or at a longitudinal periphery of the crotch portion is 7 to 35 mm, particularly 10 to 32 mm and more particularly 12 to 30 mm.

Furthermore, it has proven to be advantageous if the second elasticating means have a degree of fanning out F $$F=(A-B)/B*100\%$$

of 50 to 900%, particularly of 100 to 700% and more particularly of 150 to 550%.

The degree of fanning out F is defined as the ratio of the increase in distance (A-B) to the minimum distance (B) in percent. The variables A and B are defined here as the distance of the outermost second elasticating means in the longitudinal direction from the innermost second elasticating means in the longitudinal direction (that is to say not the spacing of second elasticating means lying directly next to one another), to be precise A as the maximum distance, particularly at the longitudinal periphery of the crotch portion or at the periphery of the absorbent body, and B as the minimum distance particularly in the side seam region. It has also been recognized that it proves to be advantageous if the degree of fanning out F of the second elasticating means is greater in the back portion than in the stomach portion.

On account of the natural shapes of the body in the back region or stomach region of a user, it proves to be advantageous if the maximum distance between the second elasticating means at a periphery of the absorbent body is greater in the back portion than in the stomach portion.

It would be entirely conceivable for the second elasticating means to run continuously from one side seam region to the other side seam region, which particularly simplifies introduction in a continuous production process in comparison with a "cut-and-place" process. As a result of the coverage of the crotch portion with the stomach portion and with the back portion, there may, depending on the design, also be an overlapping or coverage of the bulky absorbent body with the stomach portion and/or the back portion, and consequently also with that second stomach subregion and back subregion near the leg openings in which the second elasticating means run. The bulky absorbent body in this case usually hinders elastic stretchability of the chassis materials. Furthermore, it is not necessarily advantageous if the bulky absorbent body is subjected to additional tensioning forces. It may therefore prove to be advantageous if the second elasticating means are deactivated with regard to their elastic properties in an overlapping region with the absorbent body of the crotch portion. This deactivation may be realized, for example, by a number of separating cuts through the second elasticating means in the region of the coverage with the absorbent body, while other separating methods, for example by means of ultrasonic welding or laser, are also conceivable.

Reference has already been made to the fact that irrespective of the tension conditions preferably to be brought about, the second elasticating means may be exposed to increased stretching corresponding to the path of their fanning-out profile during the production of the incontinence article and hence may be exposed to higher pretension than in a non-fanning-out region, in which said elasticating means extend substantially equidistantly to one another and in the machine direction. This increased pretension can typically emerge as a result of the introduction of the second elasticating means in a conventional stretch-bond process, which will therefore not be explained in detail.

In particular, the second elasticating means are affixed in the second stomach subregion near the leg openings and/or in the second back subregion near the leg openings such that provision is respectively made in the second stomach subregion near the leg openings and/or in the second back subregion near the leg openings for at least a first layer and a second layer, between which the second elasticating means are preferably affixed by means of an adhesive applied to the whole area of the first and/or second layer.

With regard to the overall dimensions of the incontinence article, it proves to be advantageous if the distance (C) of the crotch-facing innermost second elasticating means of the stomach portion from the corresponding crotch-facing innermost second elasticating means of the back portion is 250 to 420 mm.

The distance of the innermost, crotch-facing second elasticating means from the peripheral contour, bounding the leg openings, of the crotch-side region of the stomach portion and of the back portion that is facing the leg openings is preferably 2-40 mm, more preferably 3-30 mm, particularly preferably 4-15 mm.

The second elasticating means are preferably thread-like or band-like elasticating means, such as rubber or polyether-polyurethane or polyester-polyurethane threads, preferably elastic threads such as Lycra®, Creora® or Spandex® threads. The second elasticating means preferably have a strength of 300-1500 dtex, particularly of 500-900 dtex, more particularly of 500-600 dtex.

The second elasticating means are preferably fixed with a pretensioning of 1.5-6.0, particularly of 2.5-5.0 on the chassis-forming shell materials of the second stomach subregion and second back subregion. The pretensioning is defined as a factor of the degree of stretching with respect to the unstretched/relaxed state of the elasticating means.

The extent of the stomach portion in the side seam region with a length B in the longitudinal direction and the extent of the back portion in the side seam region with a length R in the longitudinal direction is advantageously at least 100 mm, particularly at least 150 mm and particularly 150 mm to 220 mm.

The extent of the first stomach subregion away from the leg openings in the side seam region with a length B1 in the longitudinal direction is advantageously at least 60 mm, particularly at least 80 mm and particularly 80 mm to 160 mm. The extent of the first back subregion away from the leg openings in the side seam region with a length R1 in the longitudinal direction is advantageously at least 60 mm, particularly at least 80 mm, more particularly 80 mm to 160 mm.

The minimum distance between the stomach portion and the back portion in the longitudinal direction is advantageously 250 to 400 mm.

The maximum extent of the crotch portion in the transverse direction, that is to say the greatest width E, is advantageously at least 200 mm, particularly 200 to 350 mm, more particularly 250 to 320 mm. The crotch portion advantageously has the greatest width of the crotch portion within the overlapping regions of crotch portion with stomach portion and/or back portion.

As a result of the crotch portion being embodied with a very overhanging width in the transverse direction of at least 200 mm, to be precise particularly in the overlapping region, it is possible advantageously to achieve a stable connection between the crotch portion and the stomach portion and/or back portion.

Furthermore, it proves to be advantageous if the overhang of the backsheet material and/or of the topsheet material in the transverse direction is in total, that is to say on both sides of the longitudinal peripheries of the absorbent body, at least 25%, particularly 25-50%, more particularly 30-45% and more particularly 35-45% with respect to the greatest width E of the crotch portion.

The relatively large overhang of backsheet material and/or topsheet material on both sides of the absorbent body therefore means a wide crotch portion with a relatively narrow absorbent body. As a result, this realizes a large overlapping region first between crotch portion and stomach portion and secondly between crotch portion and back portion. This makes it possible to provide in the crotch portion leg elasticating means that are made to extend along the leg openings and are at a relatively great distance from the bulky, and therefore rigid, absorbent body. This in turn results in good sealability and adaptability of the leg opening peripheries on both sides of the crotch portion. This is because the bulky absorbent body that is torsionally rigid in comparison with thin chassis materials is in this way of only little hindrance to the forming of a liquid-tight leg termination; it is therefore not necessary to work with extremely high tensions to form a liquid-tight leg termination, which in turn has a positive effect on the wearing comfort of the incontinence article.

Advantageously, the topsheet material and/or the backsheet material additionally form an overhang in the longitudinal direction, which respectively extends outside of transverse peripheries of the absorbent body.

Advantageously, the backsheet material and the topsheet material have the same extent in the transverse direction and, optionally, in the longitudinal direction. They are congruous, i.e. congruent, with respect to one another.

However, it is furthermore also advantageous if the backsheet material and topsheet material are not congruous to one another. More particularly, the backsheet material advantageously has a narrower extent in the transverse direction and/or in the longitudinal direction in comparison to the topsheet material. As a result, the backsheet material, such as e.g. a sheeting, which may interfere with the wearing comfort of the user, is covered by the topsheet material, which more particularly is a nonwoven material.

The chassis-forming materials of the stomach portion and/or back portion, and hence the first and second layers of the first and second stomach subregion and/or the first and second layers of the first and second back subregion, preferably comprise nonwoven materials, such as spunbonded nonwovens (S), meltblown nonwovens (M), SM nonwovens, SMS nonwovens, SMMS nonwovens, carded nonwovens or through-air bonded carded nonwovens. Particularly preferably, the chassis-forming material of the stomach portion and/or back portion comprises spunbonded nonwoven. The nonwoven materials used for the stomach portion and/or back portion, and hence for the corresponding stomach subregions and/or back subregions, advantageously have an area density of 10-30 g/m2, more preferably of 15-25 g/m2. Particularly preferably, the stomach portion and the back portion comprise a spunbonded nonwoven of polypropylene, in particular with an area density of 15-25 g/m2.

The chassis-forming shell materials of the crotch portion are further advantageously formed: the backsheet particularly comprises a sheeting, particularly of an area density of 10-40 g/m2. In particular, the backsheet comprises a sheeting which is liquid-impermeable during use, but at the same time breathable, that is to say water-vapor-permeable, particularly microporous. The water-vapor permeability of the backsheet is particularly at least 300 g/m2/24 h, more particularly at least 1000 g/m2/24 h, more particularly at least 2000 g/m2/24 h, more particularly at least 3000 g/m2/24 h, more particularly at least 4000 g/m2/24 h, more particularly at most 6000 g/m2/24 h, measured in accordance with DIN 53 122-1 (edition: 2001-08).

The sheeting may advantageously also be provided with a nonwoven coating, which can impart a textile look to the outer side of the incontinence article that is facing away from the body. The nonwoven coating preferably consists of a nonwoven material, particularly a spunbonded nonwoven of polypropylene, particularly with an area density of 7-25 g/m2, 10-20 g/m2, particularly of 12-17 g/m2.

The topsheet material preferably comprises nonwoven materials, such as spunbonded nonwovens (S), meltblown nonwovens (M), SM nonwovens, SMS nonwovens, SMMS nonwovens, carded nonwovens or through-air bonded carded nonwovens.

The topsheet material may in this case preferably be formed only from topsheet material. More preferably, the topsheet material may be a composite of topsheet material and barrier means.

Corresponding to the functionality, advantageous materials given below are used. The topsheet material preferably comprises nonwoven materials, such as spunbonded nonwovens, carded nonwovens or through-air bonded carded nonwovens. Particularly preferably, the topsheet material comprises spunbonded nonwovens. More advantageously, the nonwoven materials used for the topsheet have an area density of 5-20 g/m2, 8-20 g/m2, more preferably of 10-18 g/m2, particularly preferably 12-16 g/m2. Particularly preferably, the topsheet comprises a hydrophilicized spunbonded nonwoven, particularly of polypropylene, particularly with an area density of 12-16 g/m2. The material of the barrier means preferably comprises nonwoven materials, such as spunbonded nonwovens, meltblown nonwovens, carded nonwovens or through-air bonded carded nonwovens. Particularly preferably, the material of the barrier means comprises single-ply or multiple-ply nonwovens. Particularly preferably, the material of the barrier means comprises laminates of one or more plies of spunbonded nonwoven (S) and/or meltblown nonwoven (M), more particularly laminates made of spunbonded nonwoven and meltblown nonwoven plies, with, in particular, a spunbonded ply as outer ply of the laminate, with, in particular, a plurality of meltblown nonwoven plies as inner plies, such as, for example, SMS-laminates, SMMS-laminates, SMMMS-laminates in particular. The meltblown or spunbonded nonwoven plies are particularly based on polyolefins, such as for example polyethylene or polypropylene. Such materials are inexpensive and, on account of their inherently hydrophobic property, suitable for having a liquid-retardant effect. More advantageously, the nonwoven materials used for the barrier means have an area density of 5-20 g/m2, preferably of 8-20 g/m2, more preferably 10-18 g/m2. Particularly preferably, the barrier means comprises a laminate of spunbonded nonwoven and meltblown nonwoven plies, particularly of polypropylene, particularly with an area density of 10-18 g/m2.

The absorbent body comprises materials that absorb body fluids, such as natural or synthetic fibers, particularly cellulose fibers, preferably in the form of cellulose fluff. The absorbent core preferably also comprises superabsorbent materials (SAP), particularly based on surface-crosslinked, partially neutralized polyacrylates.

The crotch portion or the longitudinal peripheries of the crotch portion which bound the leg openings are advantageously formed in an arcuately contoured manner.

The method according to the invention:

The method for producing incontinence articles in the form of pants for receiving bodily excretions is likewise in accordance with the invention:

The incontinence article with a front stomach portion and a rear back portion which, in order to form a stomach and back band that is continuous in the transverse or waist-encircling direction and has a waist opening closed in the waist-encircling direction, are connected to each other by the manufacturer at side seam regions on both sides. Furthermore, the incontinence article has a crotch portion having an absorbent body, wherein the crotch portion, having a stomach-side long end and a back-side long end, extends in a longitudinal direction between the stomach portion with a crotch-facing periphery and the back portion with a crotch-facing periphery.

The crotch portion overlaps the stomach portion in a front overlapping region and is joined inseparably to the stomach portion and the crotch portion overlaps the back portion in a rear overlapping region and is joined inseparably to the back portion.

The crotch portion comprises a liquid-impermeable backsheet material and a topsheet material, between which the absorbent body is arranged, wherein the topsheet material and/or the backsheet material in the transverse direction form an overhang that respectively extends outside of longitudinal peripheries of the absorbent body.

The crotch portion and also the stomach portion and the back portion delimit the leg openings of the incontinence article.

The stomach-side long end of the crotch portion extends in the longitudinal direction as far as an imaginary line L1 running parallel to the transverse direction and the back-side long end of the crotch portion extends in the longitudinal direction as far as an imaginary line L2 running parallel to the transverse direction, wherein the line L1 divides the stomach portion into a first stomach subregion away from the leg openings and a second stomach subregion near the leg openings and the line L2 divides the back portion into a first back subregion away from the leg openings and a second back subregion near the back openings.

First thread-like or band-like elasticating means with a thread diameter D are provided in the first stomach subregion and in the first back subregion and extend at a distance N from one another, and parallel to one another, in the transverse or waist-encircling direction and thus elasticate the first stomach subregion and the first back subregion across the area thereof, wherein the first stomach subregion and the first back subregion each have at least a first layer and a second layer between which the first elasticating means are secured.

The method according to the invention for securing the first elasticating means has the following method steps:
- supplying two subsidiary webs forming the respective first layer of the first stomach subregion and of the first back subregion of the incontinence article,
- supplying two subsidiary webs forming the respective second layer of the first stomach subregion and of the first back subregion,
- applying an adhesive coating, in the form of strip-shaped adhesive zones parallel in a machine direction and with a width G and at a spacing M from each other, to at least one of the two subsidiary webs forming the first stomach subregion and to at least one of the two subsidiary webs forming the first back subregion,
- supplying first elasticating means with a thread diameter D in a machine direction, parallel and at a spacing N from one another, wherein the spacing N of the supplied adjacent first elasticating means is greater than the spacing M of adjacent adhesive zones, and placing in each case a single first elasticating means in machine direction within an individual adhesive zone onto the subsidiary webs forming the first stomach subregion and forming the first back subregion,
- connecting the first elasticating means to the subsidiary webs.

In order to obtain an individual incontinence article with a three-component design, the further method steps are advantageously carried out:
- supplying crotch portions and bringing the crotch portions together with the subsidiary webs forming the first stomach subregion and with the subsidiary webs forming the first back portion in such a way that the crotch portions, in a longitudinal direction transverse to the machine direction, are arranged plane at one end with one subsidiary web and at the other end with the other subsidiary web in the front and rear overlapping region, and the crotch portions are arranged at a spacing from one another in the machine direction, and fixing the crotch portions and subsidiary webs in the overlapping regions, folding about a fold line that runs in the machine direction, in such a way that one subsidiary web comes to lie over the other subsidiary web, joining the superposed subsidiary webs transversely with respect to the machine direction at distances from one another in order to form side seam regions of the incontinence articles to be produced, and obtaining products that have a stomach portion, a back portion and, arranged between these, a crotch portion, making a separating cut transversely with respect to the machine direction and obtaining individual, finished incontinence articles.

An adhesive coating is advantageously only applied in each case to the subsidiary webs that form the first or the second layer of the first stomach subregion and of the first back subregion. The process control is simple from a technical point of view in this embodiment.

However, alternatively, it is also feasible that adhesive zones are applied to both subsidiary webs that form the first and second layer of the first stomach subregion and the first and second layer of the first back subregion. To this end, an adhesive coating in the form of adhesive zones arranged parallel to one another is applied to the facing top sides of the two subsidiary webs respectively forming the first and second layer. In the process, the subsidiary webs forming the first and second layer are provided with congruent application patterns of the adhesive coating. When the laminate with the first elasticating means is formed, these subsidiary webs are then brought into matched contact with one another with the congruent application patterns in accordance with the application pattern. In the embodiment with the adhesive coating on both subsidiary webs, use can be made of a smaller amount of adhesive, i.e. a smaller area density of the adhesive coating, per subsidiary web and per adhesive zone.

In a development of the invention, second elasticating means are supplied in addition to the first elasticating means.

Preferably, the second elasticating means are applied on the predefined subsidiary webs forming the first stomach subregion and/or the first back subregion, in an area free of first elasticating means.

As an alternative to the already predefined subsidiary webs forming the first stomach subregion and/or the first back subregion, and/or in addition thereto as well, the second elasticating means can be applied on respectively a further supplied subsidiary web forming the stomach portion and/or the back portion.

The second elasticating means are preferably supplied in such a way that they come to rest in the subsequent second stomach subregion and/or second back subregion near the leg openings.

The division of the stomach portion and back portion into a first stomach subregion away from the leg openings and a second stomach subregion near the leg openings and into a first back subregion away from the leg openings and a second back subregion near the leg openings, respectively, is obtained by arranging the crotch portion with its stomach-side long end on the stomach portion and with its back-side long end on the back portion, by virtue of an imaginary line L1 and L2 that runs parallel to the transverse direction at the respective long end, dividing the stomach portion and the back portion.

Preferably, the second elasticating means are applied to the two further subsidiary webs forming the stomach portion and back portion.

Preferably, the second elasticating means are supplied in such a way that they extend from the two side seam regions in the direction of a longitudinal center axis of the incontinence article and thereby run in an arcuately fanning-out manner with increasing distance from one another.

In order to secure the second elasticating means in the second stomach subregion near the leg openings and/or in the second back subregion near the leg openings, the subsidiary webs forming the second stomach subregion and/or the second back subregion are provided with an adhesive preferably applied to the whole surface area of the top sides facing the second elasticating means.

The subsidiary webs of the first and second layer of the subsequent first stomach subregion and/or first back subregion and/or of the second stomach subregion and/or the second back subregion are preferably made of the chassis materials and have the area densities as described above.

The first elasticating means are preferably made of the materials and preferably have the thread diameter D as described above.

Preferably, the adhesive coating is applied in form of the adhesive means and with the area densities as described above.

The adhesive zones or adhesive-zone portions are obtained by applying the adhesive coating, preferably with a width B, at a spacing M, with a length S and/or at a spacing P, as described above. The first elasticating means are preferably arranged at a spacing N from one another, as described above. Preferably, the adhesive zones or the adhesive-zone portions or the first elasticating means are arranged such that the quotients G/M, G/D and/or S/P are obtained as described above.

In order to apply the adhesive coating, the subsidiary webs that form the first and/or second layer, particularly the subsidiary webs of the subsequent first stomach subregion and first back subregion, are continuously supplied to a gluing station with a velocity v1. Preferably, the corresponding subsidiary web is guided past the gluing station by means of rollers. Advantageously, the subsidiary web is guided past the gluing station with an emergence region for the adhesive means in such a way that the subsidiary web touches the emergence region and the adhesive means is therefore applied in a contact method.

Advantageously, the emergence region of the application head is equipped with open and closed regions or can be equipped with an insertion mask with open and closed regions.

As a result of the subdivision into open and closed regions it is possible to obtain a spaced apart adhesive means emergence from the application head, which then leads to a spaced apart application of an adhesive coating in the form of strip-shaped adhesive zones when the subsidiary web is guided past. As a result of the geometry of the insertion mask or of the arrangement of the open and closed regions, the strip pattern of the adhesive zones, within the meaning of the width of the adhesive zones and the spacing of the adhesive zones from one another, can be adapted and set.

Preferably, the application head of the gluing station is equipped with metering devices for releasing desired amounts of adhesive, which can be set in a defined manner, in order to obtain advantageous area densities of the adhesive coating.

The first elasticating means are supplied in a stretched state, preferably continuously, to the respective subsidiary web. Preferably, the first elasticating means are stretched to a pretension of 1.5-6.0, preferably 2.5-5.0, preferably by means of changing the velocity over the course of supplying the elasticating means. The first elasticating means are aligned in the direction of the subsidiary web by means of commercially available thread-guiding devices and, according to the invention, respectively a single first elasticating means is positioned within an adhesive zone on the application side of the subsidiary web.

The corresponding other subsidiary web, which thus forms the second or first layer, is supplied to the process with a velocity, preferably the same velocity v1, in the web running direction and on the adhesive application side of the coated subsidiary web and after the positioning of the first elasticating means such that the first elasticating means are in the space between the subsidiary webs forming the first and second layer. The other subsidiary web is supplied directly after the application of the adhesive and the positioning of the first elasticating means such that the three materials of the laminate formation are supplied in direct succession within the setting time of the adhesive, and are pressed onto one another in the process, particularly by a roller pair. As a result of the adhesive zones which are significantly wider than the thread diameter D, this leads the two subsidiary webs to be adhered to one another in addition to the elasticating means being fixed in the adhesive bed.

Alternatively, an adhesive coating according to the process described above can likewise be applied to this further subsidiary web. In the process, the adhesive coating should be designed to be congruent with the already coated subsidiary web.

The crotch portions are preferably equipped with a topsheet material, a backsheet material and an absorbent body, and an overhang of the topsheet and/or backsheet materials extending over the longitudinal peripheries of the absorbent body, as described above.

In principle, it would be feasible for the crotch portions of the incontinence article to be supplied to be preconfigured in such a way that they are supplied continuously, particularly from a roll. According to a further method variant, it may prove to be advantageous for the crotch portions only to be formed within the continuous method by virtue of a continuous topsheet material web, a continuous backsheet material web and absorbent bodies being supplied in a machine direction and the absorbent bodies between arranged at a distance from one another between the topsheet material web and the backsheet material web and the composite formed thus is fixed in itself.

BRIEF DESCRIPTION OF THE DRAWING

Further features, details and advantages of the invention are provided by the accompanying claims and by the graphic representation and description that follows of a preferred embodiment of the incontinence article according to the invention. In the drawing:

DETAILED DESCRIPTION OF PREFERRED EMBODIMENTS

Figure 1:
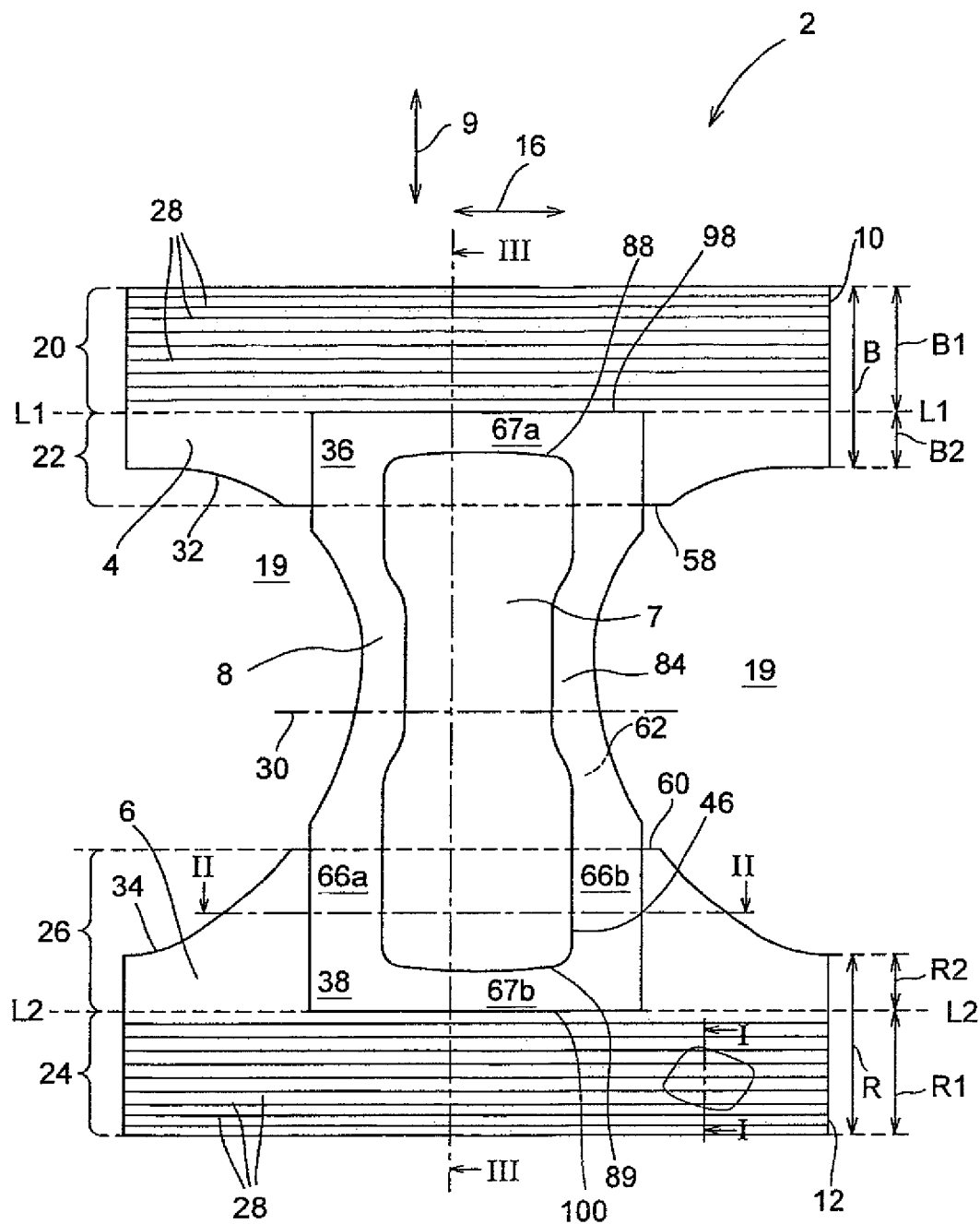
FIG. 1 shows a plan view of an incontinence article according to the invention, wherein a stomach portion, a back portion and a crotch portion, connecting the two, of the incontinence article have not yet been put together in the form of pants, but are represented in the laid-flat and stretched-out state.

The figures show an incontinence article in the form of pants, designated overall by the reference sign 2, for receiving solid and liquid bodily excretions. The incontinence article 2 is formed by three components that can, to the greatest possible extent, be produced independently of one another, to be specific a front stomach portion 4, a rear back portion 6 and a crotch portion 8, which is arranged between said stomach portion and said back portion and has an absorbent body 7, wherein the crotch portion 8 overlaps, with a substantial proportion of the surface area, the stomach portion 4 on the one hand and the back portion 6 on the other hand, and, in the overlapping region 36 of crotch portion 8 with stomach portion 4, and in the overlapping region 38 of crotch portion 8 with back portion 6, is inseparably connected by the manufacturer. As can be seen from FIG. 1, this leads to an H-shaped basic structure of the incontinence article with a longitudinal direction 9. To form the pants shape, the joined-together component parts shown in FIG. 1 are then connected to one another, likewise by the manufacturer, at respective lateral longitudinal peripheral portions 10, 12 of the stomach portion 4 and of the back portion 6, whereby side seam regions 14 are formed on both sides, as can be seen from the schematic view in FIG. 7, which shows another embodiment of the incontinence article in the form of pants (based on FIG. 6). In this state of the incontinence article in the form of pants that is produced by the manufacturer, the stomach portion 4 and the back portion 6 extend in the transverse or waist-encircling direction 16 continuously up to the side seam regions 14 and thus define a waist opening 18, which is closed in the waist-encircling direction, and leg openings 19 through which the user puts on the incontinence article like a pair of pants.

According to a preferred variant, the overlapping region 36 of crotch portion 8 with the stomach portion 4 comprises at least 12% of the surface of the stomach portion 4, and the overlapping region 38 of crotch portion 8 with the back portion 6 comprises at least 20% of the surface of the back portion 6. This proves advantageous, since in this way it is possible to achieve a secure fixing of the crotch portion 8 on the stomach portion 4 and on the back portion 6, specifically also when adhesive is not applied over the whole surface area.

The crotch portion 8, having an absorbent body 7, extends in a longitudinal direction 9 between the stomach portion 4 with a crotch-facing transverse periphery 58 and the back portion 6 with a crotch-facing transverse periphery 60 and has a stomach-side long end 98 and a back-side long end 100. The stomach-side long end 98 extends as far as an imaginary line L1 running parallel to the transverse direction 16, and the back-side long end 100 extends as far as an imaginary line L2 running parallel to the transverse direction 16. The line L1 divides the stomach portion 4 into a first stomach subregion 20 away from the leg openings and a second stomach subregion 22 near the leg openings, and the line L2 divides the back portion 6 into a first back subregion 24 away from the leg openings and a second back subregion 26 near the leg openings.

In the first stomach subregion 20 away from the leg openings and in the first back subregion 24 away from the leg openings, first elasticating means 28 are provided, these being elasticating means in the form of threads or bands, in particular such as Lycra® threads, which are connected in the pre-stretched state, in a so-called stretch-bonding process, to the chassis materials of the stomach portion 4 and of the back portion 6, as is explained in detail below with reference to FIGS. 2 and 3. These first elasticating means 28 extend from one side seam region 14 to the other in the transverse or waist-encircling direction 16.

The extent B in the longitudinal direction 9 in the side seam region 14 of the stomach portion 4 and the extent R in the longitudinal direction in the side seam region 14 of the back portion 6 is advantageously between 100 and 220 mm.

The extent B in the side seam region is composed of the extent B1 in the side seam region of the first stomach subregion 20 away from the leg openings and of the extent B2 in the side seam region of the second stomach subregion 22 near the leg openings, which extents result from the division of the stomach portion 4 by the imaginary line L1 extending in the transverse direction 16.

The extent in the longitudinal direction 9 of the first stomach subregion 20 away from the leg openings in the side seam region 14 has a length B1, which is advantageously at least 60 mm, in particular at least 80 mm, and in particular 80 mm to 160 mm.

The extent R in the side seam region is composed of the extent R1 in the side seam region of the first back subregion 24 away from the leg openings and of the extent R2 in the side seam region of the second back subregion 26 near the leg openings, which extents result from the division of the back portion 6 by the imaginary line L2 extending in the transverse direction 16. The extent in the longitudinal direction 9 of the first back subregion R1 away from the leg openings in the side seam region 14 has a length R1, which is advantageously at least 60 mm, in particular at least 80 mm, and more particularly 80 mm to 160 mm.

The extent of the crotch portion 8 in the transverse direction 16 is advantageously 200 to 350 mm.

The crotch portion 8 comprises a liquid-impermeable backsheet material 62, which may be formed particularly by a breathable, but liquid-tight sheeting material, and a topsheet material 84, preferably produced on a nonwoven basis. The absorbent body 7 is arranged between the backsheet material 62 and the topsheet material 84. The absorbent body 7 has longitudinal peripheries 46, a stomach-side transverse periphery 88 and a back-side transverse periphery 89. In the case represented by way of example, the backsheet material 62 and/or the topsheet material 84 respectively forms an overhang 66a, 66b in the transverse direction 16 on both sides of the longitudinal peripheries 46. Likewise, the backsheet material 62 and/or the topsheet material 84 respectively forms an overhang 67a, 67b on both sides of the transverse peripheries 88, 89.

Figure 4:
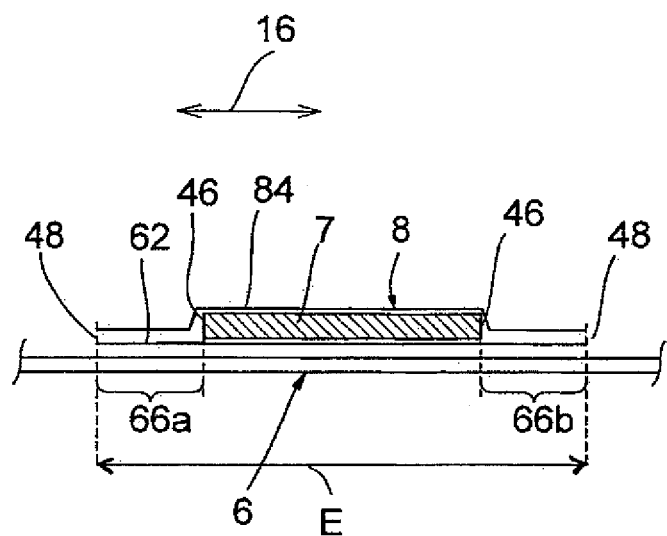
FIG. 4 shows a sectional view (schematically) along the sectional plane II-II of the incontinence article from FIG. 1.

In this connection, FIG. 4 shows a schematic sectional view of the incontinence article from FIG. 1 along the sectional plane II-II running in the transverse direction 16. The crotch portion 8, with an absorbent body 7 present between the topsheet material 84 and the backsheet material 62, overlaps the back portion 6, which comprises at least two layers. The topsheet material 84 and the backsheet material 62 extend in the transverse direction 16 outside longitudinal peripheries 46 of the absorbent body 7 and end on both sides in the longitudinal peripheries 48 of the crotch portion 8. The topsheet material 84 and backsheet material 46 form an overhang 66a, 66b on both sides. Advantageously, the overhang of the backsheet material and/or of the topsheet material in the transverse direction is in total, that is to say on both sides of the longitudinal peripheries of the absorbent body, at least 25%, in particular 25-50%, more particularly 30-45% and more particularly 35-45%, relative to the greatest width E of the crotch portion. The greatest width E is understood as the maximum extent of the crotch portion 8 in the transverse direction 16, which maximum extent is located in the present case within the overlapping region of crotch portion 8 with back portion 6.

A relatively large overhang is advantageous since, on account of the large overlapping region of crotch portion and stomach portion and of crotch portion and back portion, the crotch portion can be securely fixed to the back portion and stomach portion at the manufacturer's, in particular by means of adhesives.

Figure 6:
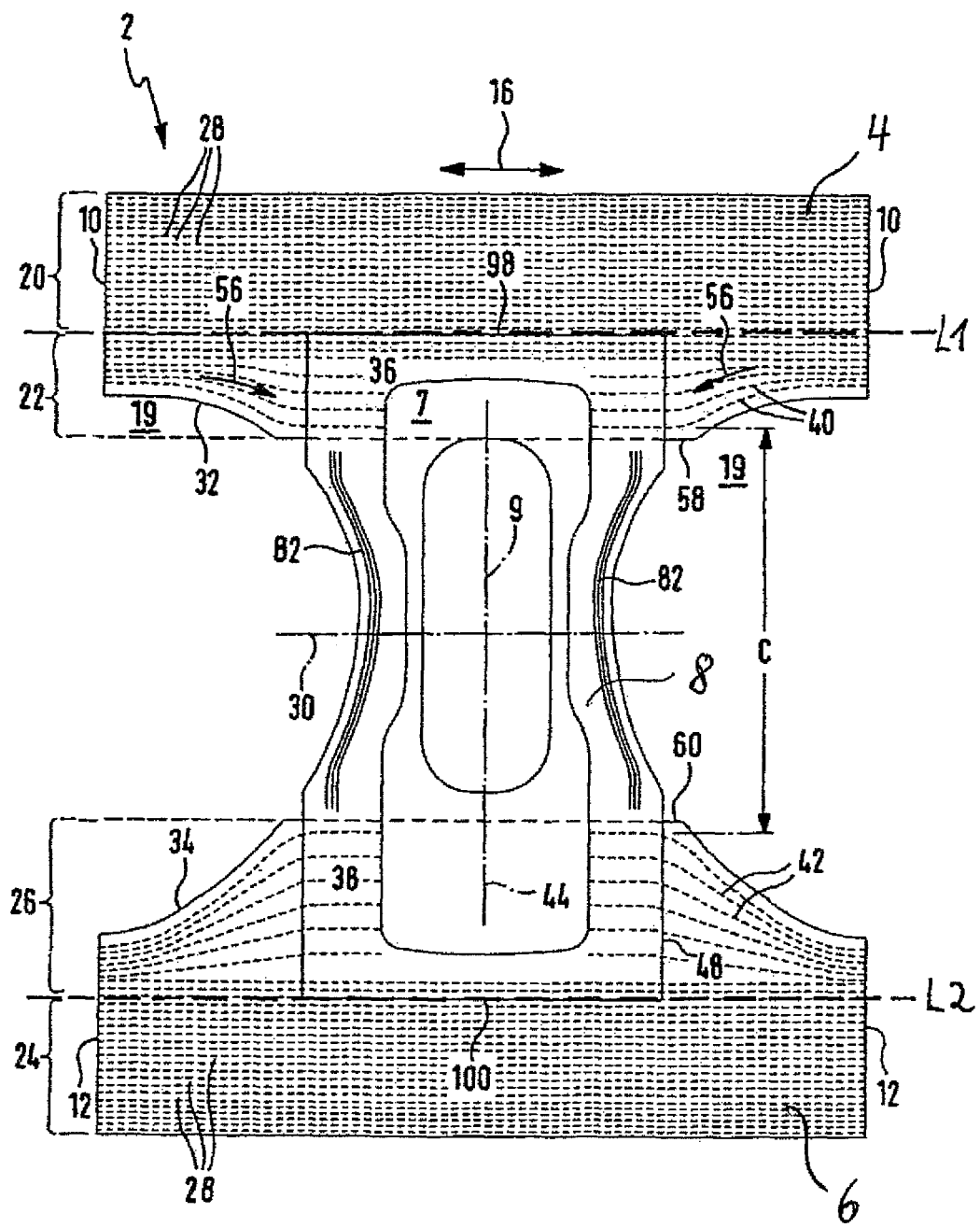
FIG. 6 shows a plan view of an incontinence article according to the invention in another embodiment, wherein a stomach portion, a back portion and a crotch portion, connecting the two, of the incontinence article have not yet been put together in the form of pants, but are represented in the laid-flat and stretched-out state.
Figure 7:
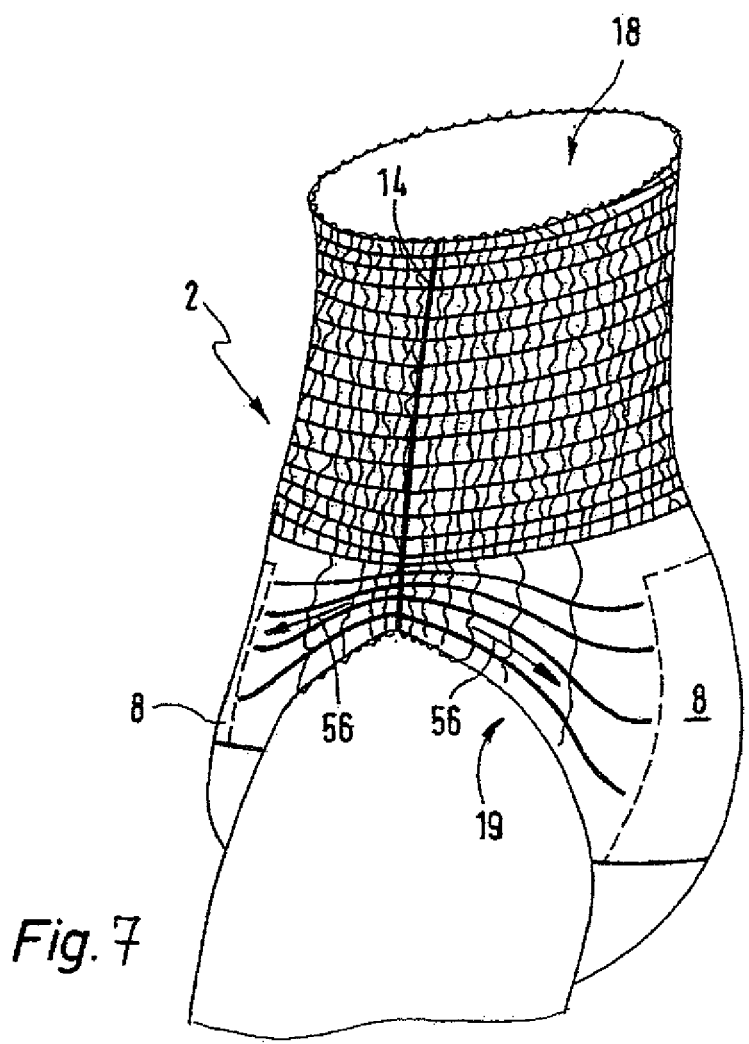
FIG. 7 shows a perspective view (schematically) of an incontinence article, in the embodiment according to FIG. 6, put onto a user.

Moreover, a large overhang in the transverse direction is advantageous for the arrangement of leg elasticating means, which are shown schematically by way of example in the embodiment according to FIG. 6 and which can also be included in the embodiment according to FIG. 1, along the leg openings 19 in the crotch portion 8.

As is shown in FIG. 6, the overhang 66a, 66b in the transverse direction 16 provides space for the arrangement of leg elasticating means 82, which extend along the leg openings 19. It proves advantageous in fact if the leg elasticating means 82 run at a certain distance from the bulky and consequently rather rigid absorbent body 7, in order on the one hand not to exert any additional stretching or torsional forces on the absorbent body, which could adversely influence its absorption behavior, and on the other hand to obtain a liquid-tight leg closure that is largely uninfluenced by the absorbent body. In the case shown, it proves to be particularly advantageous that these leg elasticating means 82 end in the longitudinal direction 9 at a clear distance of particularly at least 10 mm, preferably at least 20 mm, before the second elasticating means 40 and 42 of the stomach portion 4 and back portion 6, respectively. Preferably, these leg elasticating means 82 end in the longitudinal direction 9 before the stomach portion 4 and the back portion 6. This is advantageous and essential because the leg elasticating means 82 in this way have little or no influence on the tension-related behavior of the stomach portion 4 and of the back portion 6. As regards the aim to be advantageously achieved of improving the wearing comfort precisely in the crotch-side regions 22 and 26 of the stomach portion 4 and of the back portion 6 facing the leg openings 19, it has been found to be disadvantageous if the leg elasticating means 82, which are usually formed with great pretensioning and a correspondingly great restoring force, additionally run there.

As is shown schematically in FIG. 1, the second stomach subregion 22 near the leg openings and the second back subregion 26 near the leg openings have a peripheral contour 32 and 34, respectively, deviating from the transverse or waist-encircling direction 16 and running in the direction of a transverse center axis 30 of the crotch portion 8. This peripheral contour 32, 34 is arcuate and therefore suitable for bounding the leg openings 19. This profile of the second stomach subregion 22 near the leg openings and of the second back subregion 26 also creates a relatively great overlapping region 36, 38 between the crotch portion 8 and the stomach portion 4 or the back portion 6, which is essential with regard to a tear-resistant connection of the crotch portion 8 and the stomach portion 4 or back portion 6.

Figure 5:
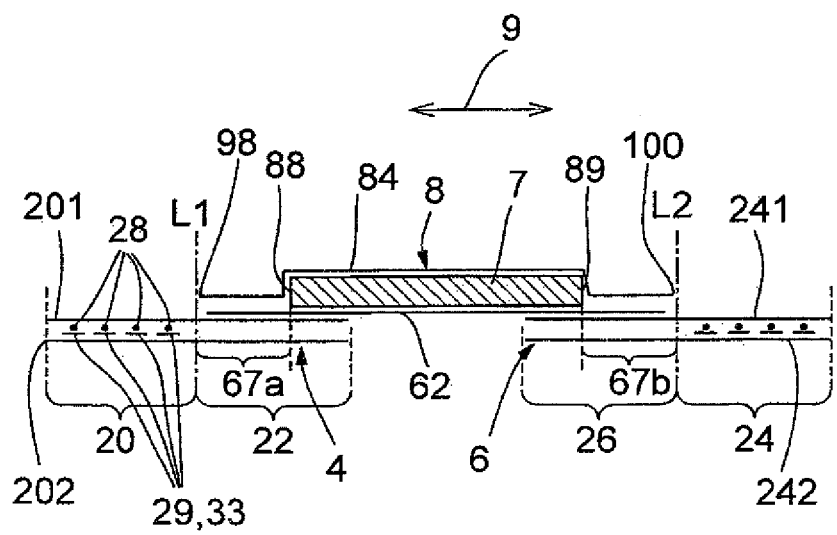
FIG. 5 shows a sectional view (schematically) along the sectional plane of the incontinence article from FIG. 1.

The sectional view of the incontinence article 2 resulting from the sectional plane along the longitudinal direction 9 in FIG. 1 is shown schematically in FIG. 5. The crotch portion 8 extends in the longitudinal direction 9 between stomach portion 4 and back portion 6 and overlaps these two components. The crotch portion 8 has a stomach-side long end 98 and a back-side long end 100, wherein an imaginary line at the long end in each case divides the stomach portion and the back portion. The stomach-side long end 98 extends as far as an imaginary line L1, which divides the stomach portion 4 into a first stomach subregion 20 away from the leg openings and a second stomach subregion 22 near the leg openings. The back-side long end 100 extends as far as an imaginary line L2, which divides the back portion 6 into a first back subregion 24 away from the leg openings and a second back subregion 26 near the leg openings. This sectional view also shows the overhangs 67a and 67b resulting from the extent of the top-sheet material 84 and backsheet material 62 outside the respective transverse periphery 88, 89 of the absorbent body 7. The first stomach subregion 20 and the first back subregion 24 each have a first layer 201, 241 and a second layer 202, 242. First elasticating means 28 are arranged between the first and second layers of the first stomach subregion 20 and of the first back subregion 24. The laminate composed of first layer, second layer and elasticating means is obtained by means of the adhesive coating 33 present in the adhesive zones 29. The arrangement of the adhesive zones and of the first elasticating means is explained in more detail with reference to FIGS. 2 and 3.

Figure 2:
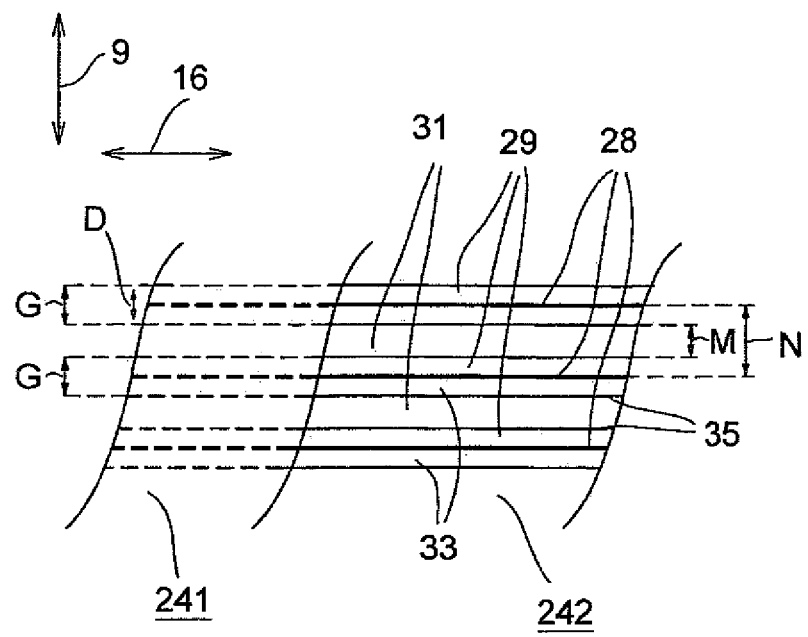
FIG. 2 shows a plan view of a detail of the back portion from FIG. 1, with depiction of adhesive zones.

FIG. 2 shows a schematic and enlarged view of a detail I-I of the first back subregion 24 away from the leg openings according to FIG. 1.

The first back subregion 24 comprises a first layer 241 and a second layer 242, between which the first elasticating means 28 are introduced. To fix the first elasticating means 28, strip-shaped adhesive zones 29 with an adhesive coating 33 are applied to the second layer 242. The adhesive zones extend in the transverse direction 16 of the first back subregion and are arranged parallel in the longitudinal direction 9 with a spacing M. The strip-shaped adhesive zones 29, limited by the peripheries 35 extending in the transverse direction 16, have a width G. The spacing M between the strip-shaped adhesive zones 29 is measured by the distance of the peripheries 35, extending adjacently in the transverse direction 16, from directly adjacent adhesive zones 29. A surface 31 free of adhesive zones remains between the strip-shaped adhesive zones 29. Within each strip-shaped adhesive zone 29, only a single thread-shaped or band-shaped first elasticating means 28 with a thread diameter D is introduced, wherein the thread diameter D is always smaller than the width G of the strip-shaped adhesive zone 29. The spacing N of the first elasticating means 28 (measured as the distance between directly adjacent first elasticating means 28) is therefore also always greater than the spacing M between the respective adjacent strip-shaped adhesive zones 29.

It is also conceivable that, instead of the first layer 241, the second layer 242 has adhesive zones with adhesive coating (not shown). Alternatively, it is likewise possible that both the first layer 241 and also the second layer 242 have adhesive zones with adhesive coating (not shown). In the latter case, it is advantageous if the first layer and the second layer have a congruent pattern of applied adhesive zones which, upon formation of the laminate, are then arranged particularly preferably in a coincident manner over each other.

Figure 3:
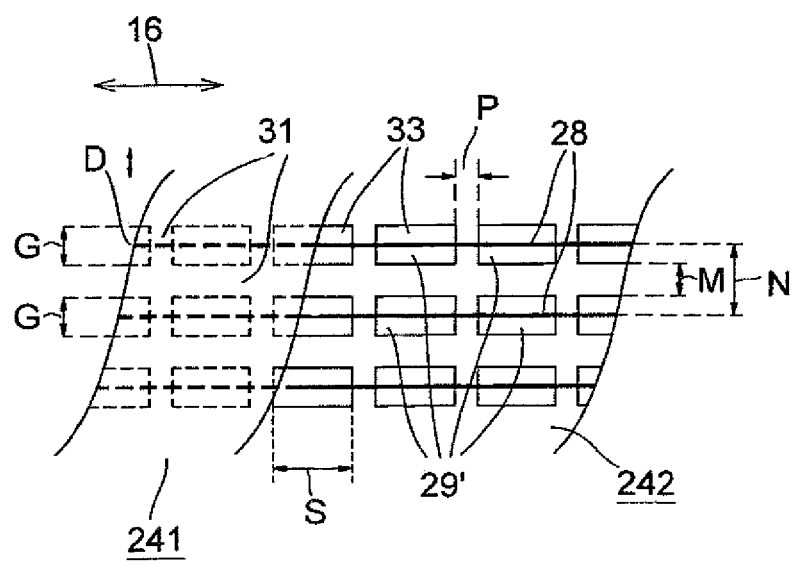
FIG. 3 shows a view similar to FIG. 2, with an alternative design of the adhesive zones.

FIG. 3, likewise an enlarged and schematic view of the detail I-I from FIG. 1, shows, analogously to FIG. 2, first elasticating means 28 introduced individually between a first layer 241 and second layer 242 within adhesive zones, but in an alternative embodiment, such that the strip-shaped adhesive zones 29 comprise adhesive-zone portions 29' arranged at a spacing P in the transverse direction 16. The adhesive-zone portions 29' have a length S which, in the transverse direction 16, is advantageously greater than the spacing P. In particular, the quotient S/P is at least 0.1, but preferably at most 15. The adhesive-zone portions advantageously have a length S of at least 2 mm and at most 30 mm. The spacing P of the directly adjacent adhesive-zone portions is in particular at least 2 mm, more particularly at most 20 mm.

The adhesive zones 29 or the adhesive-zone portions 29' have a width G and are arranged parallel in the longitudinal direction with a spacing M. The width G of the adhesive zones and the spacing M are advantageously adapted to each other. The quotient G/M is advantageously at least 0.10 and preferably at most 7.5.

The adhesive zones 29 or the adhesive-zone portions 29' advantageously have a width G of between 2 and 15 mm and are advantageously arranged parallel at a spacing M of between 2 and 25 mm. The first elasticating means 28 have a thread diameter D smaller than the width G of the adhesive zones or adhesive-zone portions, advantageously such that the quotient G/D is at least 2 and at most 100. It is particularly advantageous to use elasticating means with a thread diameter D of 0.05-1.0 mm. The adhesive coating 33 within the adhesive zones 29 is applied in the form of a glue, in particular a hot-melt glue. It is particularly preferable to apply a hydrophobic glue, particularly the glue LC 3001ZP from Fuller (H. B. Fuller Deutschland GmbH, An der Roten Bleiche 2-3, 21335 Lüneburg, Germany). The adhesive coating 33 is applied in a base weight of 2-40 g/m2.

FIG. 6 shows a plan view of an incontinence article according to the invention, in a state in which it is still spread out and has not yet been connected at the longitudinal peripheries of stomach portion and back portion, and in which, in addition to having the first elasticating means 28 in the first stomach subregion 20 and in the first back subregion 24, the incontinence article 2 is also elasticated in the second stomach subregion 22 near the leg openings and in the second back subregion 26 near the leg openings. The reference signs explained in connection with FIG. 1 can be applied to FIG. 6.

Figure 8:
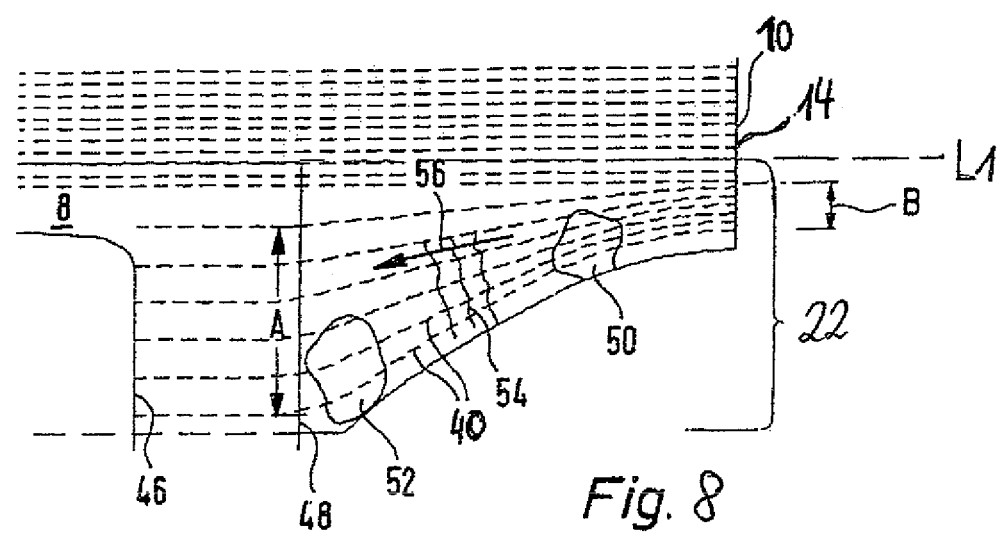
FIG. 8 shows a plan view of a detail of the stomach portion from FIG. 6.

Second elasticating means 40, 42 are provided in the second stomach subregion 22 and back subregion 26, respectively, near the leg openings. The second elasticating means 40, 42 in each case extend from the longitudinal peripheries 10, 12 of stomach portion 4 and back portion 6, respectively, in the direction of a longitudinal center axis 44 of the incontinence article. As can be seen from FIG. 6, the second elasticating means 40, 42 fan out in the direction of the longitudinal center axis 44. This means that the spacing between them increases in the direction of the longitudinal center axis 44. This fanning out of the second elasticating means 40 and 42 can also be quantitatively specified more precisely on the basis of FIG. 8. For example, the second elasticating means 40 (shown in FIG. 8) of the second stomach subregion 22 near the leg openings have, at the longitudinal peripheries 10 or side seam regions 14, a minimum spacing of 3 to 8 mm (spacing of elasticating means lying directly next to one another) and, at a periphery 46 of the absorbent body or a longitudinal periphery 48 of the crotch portion 8, have a maximum spacing (spacing of elasticating means lying directly next to one another) of 7 to 35 mm. On the basis of FIG. 8, a degree of fanning out F can also be defined as follows:

$$F=(A-B)/B*100\%$$

This degree of fanning out may advantageously lie between 50 and 900%, particularly between 100 and 700% and more particularly between 150 and 550%. It is advantageously greater in the back portion 6 than in the stomach portion 4. The variables A and B are defined here as the distance of the outermost second elasticating means 40, 42 in the longitudinal direction 9 from the innermost second elasticating means 40, 42 in the longitudinal direction 9 (that is to say not the spacing of elasticating means lying directly next to one another), to be precise A as the maximum distance, particularly at the longitudinal periphery 48 of the crotch portion 8, and B as the minimum distance, particularly in the side seam region 14 (cf. FIG. 8).

If the degree of fanning out chosen for the second elasticating means 40, 42 is sufficiently great, it is possible in this way to obtain a decreasing restoring force within the second stomach subregion 22 near the leg openings, or within the second back subregion 26 near the leg openings, in the direction 56 of the crotch portion 8, as long as it is ensured that the arcuate shape of the second elasticating means 40, 42 that is facing away from the waist or transverse direction 16 does not cause an excessive increase in the pretensioning as a result of the greater path followed by these second elasticating means 40, 42. If an area 50, lying closer to the side seam region 14, of the second stomach subregion 22 or back subregion 26 near the leg openings is considered along with an area 52 lying closer to the crotch portion 8, the restoring force that occurs upon stretching over the surface of the area 52 (stretching in the direction of the elasticating means 42) is less than the restoring force that occurs upon stretching of the area 50. This advantageously also has the effect that, as a result of the lower elastic forces that are exerted by the second elasticating means 40, 42 in the case shown by way of example, the chassis materials of the stomach portion 4 and of the back portion 6 are gathered to a lesser extent, such that a smaller number of folds/ruffles 54 also occurs, to be precise from the respective side seam region 14 in the direction of the crotch portion 8. The fact that the restoring forces occurring upon stretching over the surface area of the second stomach subregion 22 near the leg openings, or of the second back subregion 26 near the leg openings, decrease in the direction of the arrow 56, that is to say generally from the side seam region 14 in the direction of the crotch portion 8, means that a considerable improvement in the wearing comfort is achieved, because—as has been established—elastically stretchable materials prove to be particularly problematic in precisely these regions, because these materials are especially subjected to pulling and stretching in a way corresponding to the physiognomy of the human anatomy in these regions. A deliberate and advantageous reduction in this restoring force, that is to say a decreasing restoring force in the direction of the arrow 56, that is to say in the direction of increasing proximity to the crotch portion 8, has the effect here of providing a hitherto unachieved degree of freedom.

Figure 9:
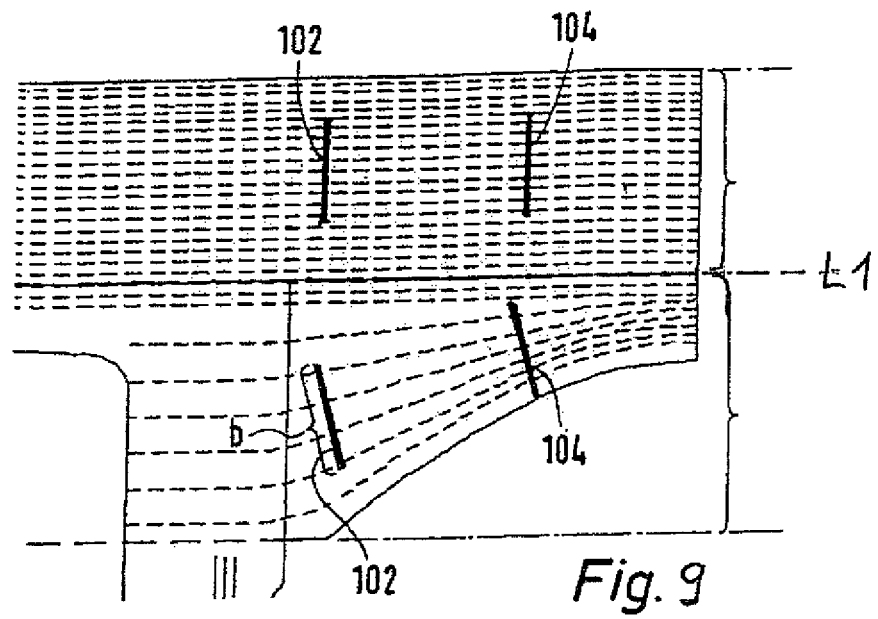
FIGS. 9, 10 illustrate, by way of example, the determination of restoring forces in the stomach portion and back portion, respectively, of the incontinence article.
Figure 10:
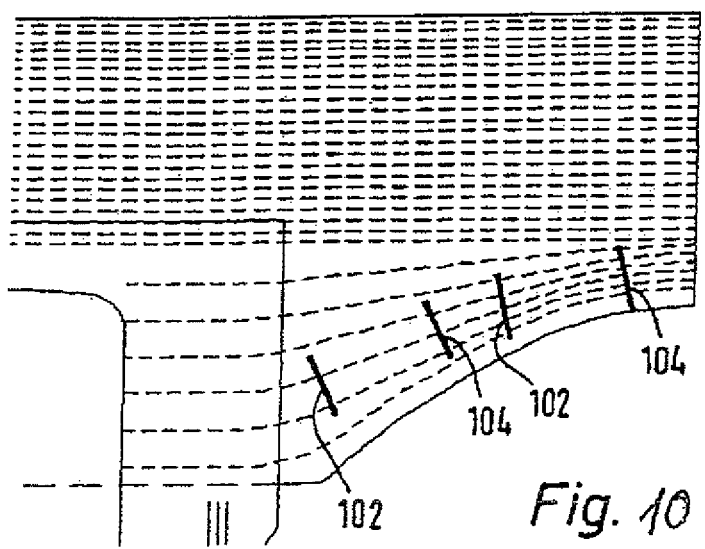

As was stated at the outset, restoring forces may be determined directly on the chassis of the incontinence article. For this, the region concerned of the stomach portion 4 or of the back portion is clamped between two clamping jaws 102, 104 (see FIGS. 9 and 10) with a defined and identical clamping jaw width (b), and restoring forces are then determined under defined stretching of the regions to be measured that simulates the state of use, by particularly 30% or 50% or 80% of the initial length (of the clamping jaw spacing in the unclamped state). The clamping jaws 102, 104 are in this case respectively moved away from each other. The clamping jaws 102, 104 should fix as many elasticating means 28, 40, 42 as possible, but at least two arranged next to each other, of the region to be measured, and they should be oriented substantially perpendicularly with respect to the line followed by the elasticating means, such that the stretching between the clamping jaws 102, 104, that is to say the moving apart of the clamping jaws 102, 104, takes place substantially in the direction of the line followed by the elasticating means. This is realized in FIGS. 9 and 10.

In the preferred embodiment of the incontinence article 2 that is shown, a distance C of the crotch-facing innermost second elasticating means 40 of the stomach portion 4 from the corresponding crotch-facing innermost second elasticating means 42 of the back portion 6 is between 250 and 420 mm, depending on the manufactured size of the incontinence article. The second elasticating means 40, 42 extend substantially as far as the crotch-facing transverse periphery 58, 60 of the stomach portion 4 and of the back portion 6. The distance between stomach portion 4 and back portion 6 is 250-400 mm.

The distance of the innermost, crotch-facing second elasticating means 40, 42 from the peripheral contour 32, 34, bounding the leg openings, of the second stomach subregion 22 and back subregion 26 near the leg openings is preferably 2-40 mm, more preferably 3-30 mm, particularly preferably 4-15 mm.

Figure 11A:
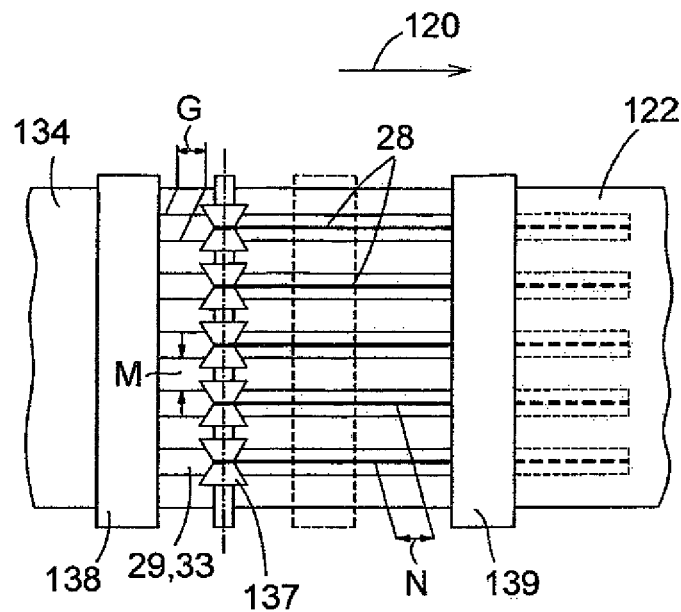
FIGS. 11*a*, 11*b*, 11*c* show a schematic view of the method according to the invention for fixing the first elasticating means.
Figure 11B:
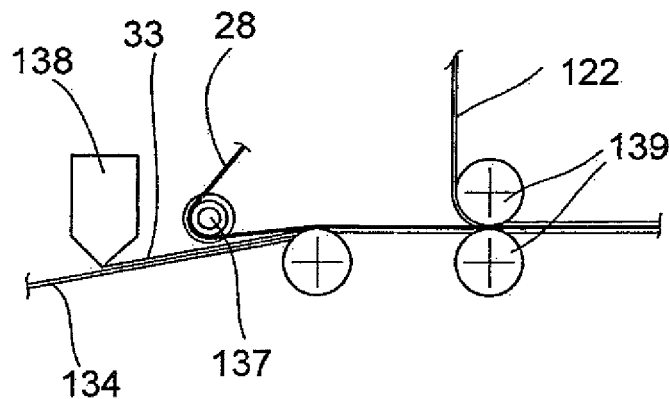
Figure 11C:
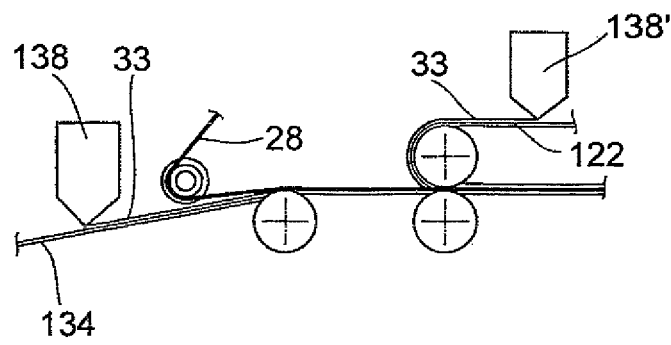
Figure 12:
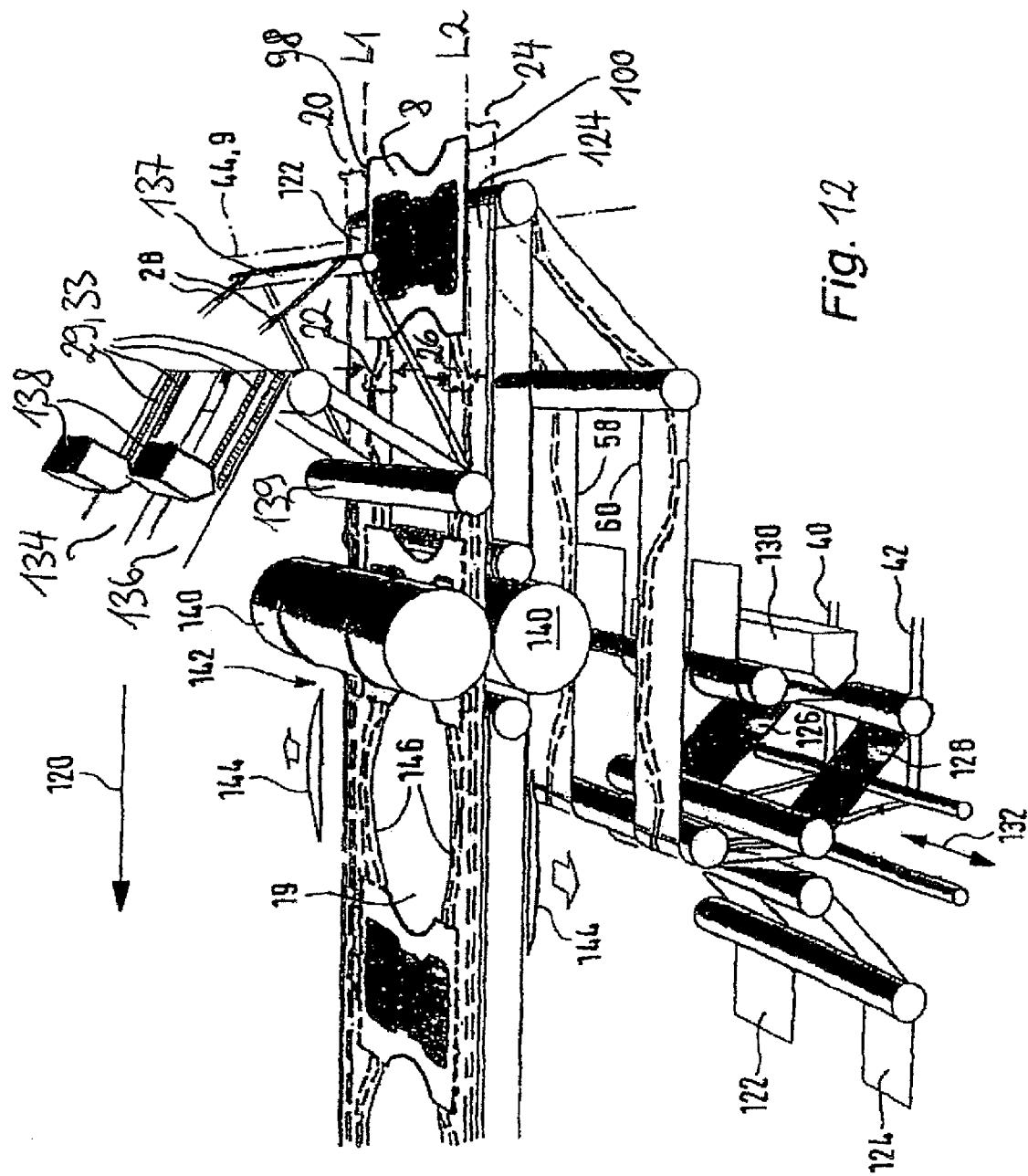
FIG. 12 shows a schematic view of the supply and attachment of elasticating means to the first and second stomach subregion or back subregion.
Figure 13:
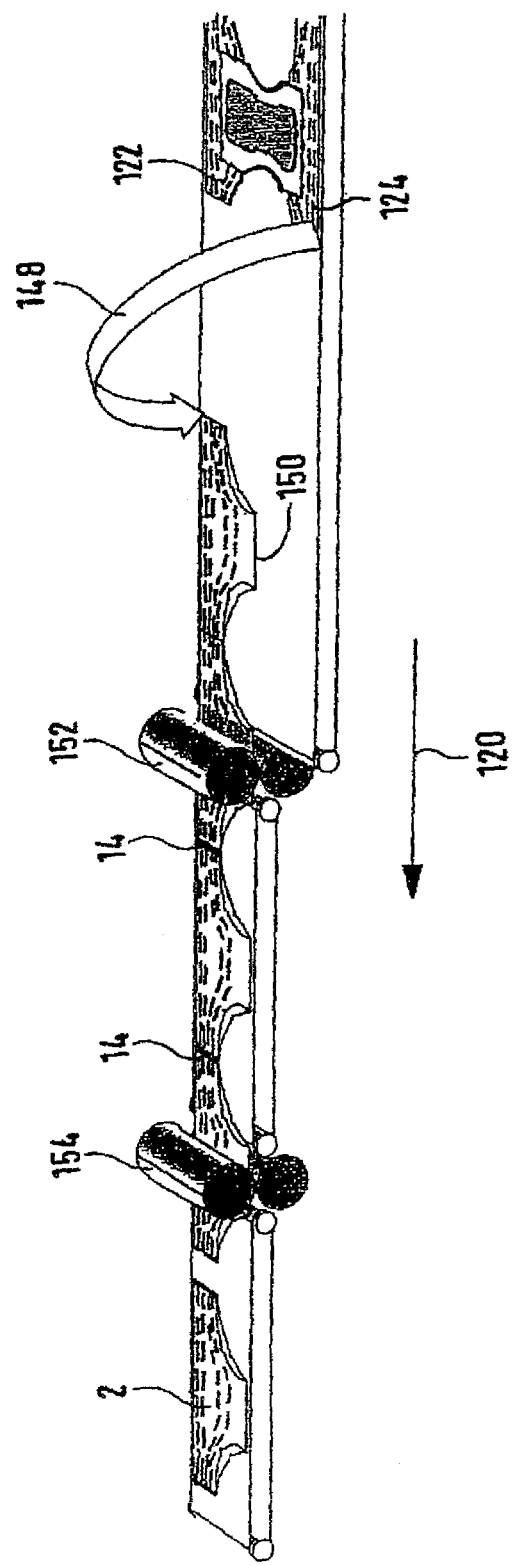
FIG. 13 shows a schematic view of the folding into the form of pants, and the formation of side seam regions and subsequent individualization of the hygiene articles.

Method according to the invention:

FIGS. 11 to 13 show the method of production according to the invention.

As can be seen from FIG. 12, subsidiary webs 122, 124, preferably based on nonwovens, are supplied in order to produce the subsequent stomach portion 4 and back portion 6 of the incontinence article 2, in a state, as shown in FIG. 1 or 4, in which the incontinence article is still spread out and has not yet been connected at the longitudinal peripheries of stomach portion and back portion. These subsidiary webs 122, 124 can be formed from a single web, by separation in the longitudinal direction.

These subsidiary webs 122, 124 are brought together with crotch portions 8, specifically in such a way that the crotch portions, extending in a longitudinal direction 9 transverse to the machine direction 120, overlap one subsidiary web 122 at one end and overlap the other subsidiary web 124 at the other end. The crotch portion 8 has a stomach-side long end 98 and a back-side long end 100. These long ends 98, 100 extend as far as a parallel imaginary line L1, L2, respectively. With the imaginary line L1, the subsidiary web 122 forming the subsequent stomach portion is divided into a first stomach subregion 20 away from the leg openings and a second stomach subregion 22 near the leg openings. Analogously, with the imaginary line L2, the subsidiary web 124 forming the subsequent back portion is divided into a first back subregion 24 away from the leg openings and a second back subregion 26 near the leg openings.

Further subsidiary webs 134, 136, in particular on a nonwoven basis, are supplied, which are likewise provided for the formation of the subsequent stomach portion and back portion.

Furthermore, the first elasticating means 28 extending in the transverse or waist-encircling direction 16 and provided for fixing in the subsequent first stomach subregion and in the subsequent first back subregion are then supplied continuously in the machine direction 120. In particular, the first elasticating means are supplied via thread-guiding devices 137 in a manner spaced apart from each other and with pretensioning. In order to fix the first elasticating means 28 between the interacting subsidiary webs 122, 134 for forming the stomach portion, and therefore the first stomach subregion 20, and between the subsidiary webs 124, 136 for forming the back portion, and therefore the first back subregion 24, the subsidiary webs are provided with an adhesive coating 33. The adhesive coating 33 is applied in the form of strip-shaped adhesive zones 29 to the subsidiary webs. In the illustrative embodiment shown, the adhesive coating 33 is applied to in each case only one of the two subsidiary webs, here 134, i.e. to the first or second layer of the subsequent first stomach subregion, and to in each case only one of the two subsidiary webs, here 136, i.e. to the first or second layer of the subsequent first back subregion. However, alternatives are also conceivable in which the adhesive coating is applied to in each case the other of the subsidiary webs or also to both subsidiary webs, as is outlined schematically below with reference to FIGS. 11a-c.

To apply the adhesive coating 33 in strip-shaped adhesive zones 29 arranged in parallel and spaced apart in the machine direction 120, the subsidiary webs 134, 136 are guided past a gluing station 138, such that the glue is applied in particular by a contact method.

The subsidiary webs, provided with applied glue, and the first elasticating means are brought together for laminate formation, in such a way that only a single first elasticating means 28 in each case comes to lie within an adhesive zone 29 along the machine direction 120. Thereafter, the materials, i.e. the respective subsidiary webs and the elasticating means, are pressed onto each other by means of a roller 139, in particular a pair of rollers 139, within the setting time of the adhesive 33.

FIGS. 11a, b and c again illustrate the method by which stretched first elasticating means, i.e. first elasticating means provided with pretensioning, are fixed. FIG. 11a is a schematic plan view of the laminating step, on the basis of the subsequent first stomach subregion, and therefore subsidiary webs 122, 134 forming the one first layer 201 and the one second layer 202.

The gluing station 138 applies glue, as adhesive coating 33, to the subsidiary web 134 guided past it. The dispensing head of the gluing station has openings (not shown here) at a distance from one another. As the subsidiary web 134 is guided past at a defined speed in the machine direction 120, strip-shaped adhesive zones 29 with a width G are generated in parallel and at a spacing M from one another.

A thread-guiding device 137 is used to position the first elasticating means 28, individually with a spacing N and in the stretched state, above the adhesive zones 29 provided with adhesive coating 33. All materials are pressed together by means of a roller 139 while another subsidiary we 122 is being supplied.

FIGS. 11b and 11c show the process described above in a schematic side view, with FIG. 11c, as a modification thereof, illustrating in the form of a sketch the alternative of applying adhesive to both subsidiary webs 134, 122. In this case, the subsidiary web 122 with the top side facing the subsidiary web 134 is likewise guided under a gluing station 138' for applying an adhesive coating 33 and then brought together with the subsidiary web 134 and the first elasticating means 28. Advantageously, the subsidiary web 122 with an adhesive coating 33 is provided in the application pattern congruent to the subsidiary web 134 such that the first elasticating means then come to rest between the adhesive coating 33 of the subsidiary web 134 and the subsidiary web 122 and are fixed as a result of this.

FIG. 12 furthermore the introduction of second elasticating means 40, 42 for obtaining a further elasticated region of the subsequent stomach portion 4 and back portion 6 of the incontinence article 2, as illustrated in FIG. 4 in a state which is still spread out and not connected at the long peripheral portions of stomach portion and back portion.

The second elasticating means 40 and 42 are applied to these subsidiary webs 122, 124 mentioned at the outset; for this purpose they are likewise supplied continuously and in the conveying direction of the subsidiary webs 122, 124. In order to affix the second elasticating means 40, 42 on the subsidiary webs 122, 124, respectively one nonwoven cover layer 126, 128, to which adhesive was previously applied in a gluing station 130, preferably to the whole surface area, is applied such that the second elasticating means 40, 42 are laminated between the subsidiary webs 122, 124 and the nonwoven cover layers 126, 128. Although this is not visible in FIG. 12 as a result of the schematic illustration, the second elasticating means 40, 42 are supplied with a varying spacing from one another, which is realized by an oscillating guide apparatus that is indicated by the double-headed arrow 132. Thus, appropriate actuation of the guiding apparatus forms the arcuately fanning-out profile of the second elasticating means 40, 42 in the direction of the crotch portion 8 for each individual elasticating means 40, 42. Here, the second elasticating means 40, 42 are supplied such that they come to rest on the subsidiary webs within the subsequent second stomach subregion 22 and the subsequent second back subregion 26.

However, it would possibly also be feasible for the elasticating means 40 and 42 all to be provided with adhesive individually, that is to say for these to be glued like a thread.

It would possibly also be feasible for it to be possible to dispense with the nonwoven cover layers 126 and/or 128, independent of the type of adhesive-means application onto the elasticating means 40 and 42. However, the nonwoven cover layers are advantageous in that they at the same time form an inner side of the incontinence article that feels soft.

It is also the case in the embodiment with the second elasticating means 40, 42 that the crotch portions 8 are supplied such that they are arranged with a spacing from one another in the machine direction 120 after being brought together. In the configuration obtained from FIG. 12, the crotch portions 8 and the subsidiary webs 122, 124 are fixed to one another and conveyed on in the machine direction 120 and equipped with the first elasticating means 28, as already described above.

Following this, provision is made in FIG. 12 for a cutting roller pair 140, that is to say a rotating knife with an anvil roller, between which the previously formed composite is guided though in the machine direction 120 and with the described orientation. In the process, a contour cut 142 is carried out, within the scope of which respectively one arcuate segment 144 is severed, preferably only from the subsidiary webs 122, 124, and to be precise only from the transverse peripheries or peripheral portions 58 and 60 facing one another of the subsidiary webs 122, 124 such that leg cutouts 146 are also formed in the subsidiary webs 122, 124. As a result of the fact that the contour cut 142 does not encompass the crotch portion 8 but only the subsidiary webs 122, 124, the contour cut 142 runs substantially along the machine direction 120 and in any case not transversely at a large angle thereto. This allows the cut to be configured in an optimal manner. Overall, this enables the subsequent leg openings 19 of the incontinence article 2 to be embodied with great accuracy in accordance with the requirements considered to be optimal. In the process, it proves to be advantageous that the contour cut 142 can be embodied with a different profile on the subsidiary web 122 than on the subsidiary web 124. As a result, the form of the leg cutouts 146 and the subsequent leg openings 19 of the incontinence article 2 can have different configurations in the stomach portion 4 and in the back portion 6.

The composite configured thus is conveyed on, and the composite is folded onto itself about a fold line 150 running in the machine direction 120 in a folding station 148 only indicated in FIG. 13 such that the one subsidiary web 124 comes to rest over the other subsidiary web 122. Following this, a respective side seam region 14 is formed between the subsidiary webs 122, 124 in a joining station 152, that is to say the actual pants form is formed. Following this method step, a separation cut transversely to the machine direction 120 is brought about in a separating station 154 and this leads to the individualization of the finished incontinence articles 2. It would also be feasible for the joining station 152 to be embodied as a separating station at the same time, for example in the form of a weld and tear apparatus such that the incontinence articles 2 are individualized together with the formation of the side seam region 14.

The method steps sketched in FIG. 13 should also be applied to the embodiment of the incontinence article with only first elasticating means, that is to say without second elasticating means.

In principle, it would be feasible for the crotch portions 8 of the incontinence article to be supplied to be preconfigured in such a way that they are supplied continuously, particularly from a roll. According to a further method variant, it may prove to be advantageous for the crotch portions only to be formed within the continuous method by virtue of a continuous topsheet material web, a continuous backsheet material web and absorbent bodies being supplied in a machine direction and the absorbent bodies being arranged at a distance from one another between the topsheet material web and the backsheet material web and the composite formed thus is fixed in itself.

The invention claimed is:

1. An incontinence article in the form of pants for receiving bodily excretions, comprising:
  a front stomach portion having adjacent first and second stomach subregions defined by a first imaginary line extending parallel to a transverse direction of the incontinence article, said front stomach portion having a first crotch facing transverse periphery, wherein the first stomach subregion is distal from leg openings of the incontinence article and the second stomach subregion is proximate to the leg openings;
  a rear back portion arranged separate and spaced apart from the front stomach portion by a free space and having adjacent first and second back subregions defined by a second imaginary line extending parallel to the transverse direction, wherein the first back subregion is distal from the leg openings and the second back subregion is proximate to the leg openings, said rear back portion having a second crotch facing transverse periphery, wherein the first stomach subregion and the first back subregion each have at least one first layer, at least one second layer and first thread-like or band-like elasticating means for elasticating the first stomach subregion and the first back subregion across a surface area of the first stomach subregion and the first back subregion, said first elasticating means having a thread diameter and extending in the transverse direction, at a distance to one another, and parallel to one another, wherein the first elasticating means are secured between the at least one first and one second layers by strip-shaped adhesive zones provided respectively in the first stomach subregion and the first back subregion, said strip-shaped adhesive zones having a width in a longitudinal direction of the incontinence article which is greater than the thread diameter, said strip-shaped adhesive zones running parallel in the transverse direction, and being arranged at a distance M from one another in the longitudinal direction, and wherein not more than a one of the elasticating means is arranged within each of the strip-shaped adhesive zones; and
  a crotch portion comprising an absorbent body, a liquid-impermeable backsheet material and a topsheet material, and having a stomach-side long end and a back-side long end, wherein the absorbent body is arranged between the backsheet material and the topsheet material, wherein the topsheet material and/or the backsheet material form an overhang which extends outside of longitudinal peripheries of the absorbent body, wherein the crotch portion extends in the longitudinal direction of the incontinence article between the stomach portion and the back portion, said stomach-side long end extending up to the first imaginary line, and said back-side long end extending up to the second imaginary line, wherein the crotch portion overlaps the stomach portion in a front overlapping region and is joined inseparably to the stomach portion, wherein the crotch portion overlaps the back portion in a rear overlapping region and is joined inseparably to the back portion, wherein the crotch portion, the stomach portion and the back portion delimit the leg openings of the incontinence article, and wherein the stomach portion and the back portion have opposing side seam regions and are connected to each other at the side seam regions to form a stomach- and back band which is continuous in a waist-encircling direction of the incontinence article thereby defining a waist opening.

2. The incontinence article of claim 1, wherein said width of the adhesive zones divided by said distance of the adhesive zones to one another equals at least 0.10, and at most 5.0.

3. The incontinence article of claim 1, wherein said width of the adhesive zones divided by said thread diameter equals at least 2, and at most 100.

4. The incontinence article as of claim 1, wherein the strip-shaped adhesive zones comprise adhesive zone portions having a length S in the transverse direction of the incontinence article and being arranged at a spacing P in the transverse direction, said adhesive zone portions being preferably arranged in such a way that the length S divided by the spacing P equals at least 0.1, and at most 15.

5. The incontinence article of claim 1, wherein the first stomach subregion and/or the first back subregion occupy a proportion of 30-75%, more particularly of 35-70%, relative to the surface area of the stomach portion and/or of the back portion.

6. The incontinence article of claim 1, wherein 20-80%, of the surface area of the first stomach subregion and/or of the first back subregion is free from adhesive zones and/or adhesive zone portions.

7. The incontinence article of claim 1, wherein the adhesive zones and/or adhesive zone portions have an adhesive coating with an area density of 2-40 g/m$^2$.

8. The incontinence article of claim 7, wherein the adhesive coating is applied to the first and/or second layer of the first stomach subregion and to the first and/or second layer of the first back subregion.

9. The incontinence article of claim 1, wherein said front overlapping region occupies at least 12%, and up to 40%, of the stomach portion, and said rear overlapping region occupies at least 20%, and up to 40%, of a surface of the back portion.

10. The incontinence article of claim 1, wherein the overhang of the backsheet material and/or of the topsheet material in the transverse direction is on both sides of the longitudinal peripheries of the absorbent body, 25-50%, relative to a maximal width of the crotch portion.

11. The incontinence article of claim 1, wherein the second stomach subregion and/or in the second back subregion further comprise second elasticating means.

12. The incontinence article of claim 11, wherein the second elasticating means extend from each of the two side seam regions in a direction of a longitudinal center axis of the incontinence article in an arcuately fanning-out manner, and with an increasing distance to one another.

13. The incontinence article of claim 11, wherein the second stomach subregion and the second back subregion each have at least a first layer and a second layer, wherein the second elasticating means are secured between the first and second layers, in particular by means of an adhesive coating applied over an entire surface of the first and/or second layer.

* * * * *